(12) United States Patent
Huang et al.

(10) Patent No.: US 11,401,344 B2
(45) Date of Patent: *Aug. 2, 2022

(54) METHODS FOR DETERMINING THE LIKELIHOOD OF SURVIVAL AND FOR PREDICTING LIKELIHOOD OF METASTASIS IN CANCER PATIENTS

(71) Applicant: Laboratory Corporation of America Holdings, Burlington, NC (US)

(72) Inventors: Weidong Huang, Pleasanton, CA (US); Jodi Weidler, Foster City, CA (US); Jeff Sperinde, El Granada, CA (US); Mojgan Haddad, Orinda, CA (US); Michael Bates, San Carlos, CA (US); John William Winslow, El Granada, CA (US); Xueguang Jin, Fremont, CA (US); Gerald J. Wallweber, Foster City, CA (US); Jennifer W. Cook, San Mateo, CA (US); Gundo Diedrich, South San Francisco, CA (US); Laurie Goodman, El Granada, CA (US); Ali Mukherjee, Millbrae, CA (US); Gordon Parry, Oakland, CA (US); Stephen J. Williams, San Carlos, CA (US)

(73) Assignee: Laboratory Corporation of America Holdings, Burlington, NC (US)

(*) Notice: Subject to any disclaimer, the term of this patent is extended or adjusted under 35 U.S.C. 154(b) by 82 days.

This patent is subject to a terminal disclaimer.

(21) Appl. No.: 16/166,878

(22) Filed: Oct. 22, 2018

(65) Prior Publication Data

US 2019/0055319 A1 Feb. 21, 2019

Related U.S. Application Data

(60) Continuation-in-part of application No. 15/681,895, filed on Aug. 21, 2017, now Pat. No. 10,775,382, which is a continuation of application No. 14/802,170, filed on Jul. 17, 2015, now Pat. No. 9,766,242, application No. 16/166,878, which is a continuation-in-part of application No. 14/737,742, filed on Jun. 12, 2015, now Pat. No. 10,273,308, which is a continuation of application No. 13/911,329, filed on Jun. 6, 2013, now Pat. No. 9,081,019, which is a continuation of application No. 13/670,508, filed on Nov. 7, 2012, now Pat. No. 9,110,066, application No. 16/166,878, which is a continuation-in-part of application No. 13/476,735, filed on May 21, 2012, now abandoned, said application No. 13/670,508 is a continuation-in-part of application No. 12/688,798, filed on Jan. 15, 2010, now Pat. No. 8,349,574, said application No. 13/911,329 is a division of application No. 12/629,037, filed on Dec. 1, 2009, now Pat. No. 8,470,542.

(60) Provisional application No. 61/488,028, filed on May 19, 2011, provisional application No. 61/187,962, filed on Jun. 17, 2009, provisional application No. 61/187,960, filed on Jun. 17, 2009, provisional application No. 61/182,282, filed on May 29, 2009, provisional application No. 61/176,630, filed on May 8, 2009, provisional application No. 61/145,029, filed on Jan. 15, 2009, provisional application No. 61/118,975, filed on Dec. 1, 2008.

(51) Int. Cl.

| | |
|---|---|
| G01N 33/574 | (2006.01) |
| C07K 16/32 | (2006.01) |
| G01N 33/50 | (2006.01) |
| G01N 33/68 | (2006.01) |
| A61P 35/00 | (2006.01) |
| G01N 33/74 | (2006.01) |
| C12Q 1/6886 | (2018.01) |
| A61K 45/06 | (2006.01) |
| A61K 39/00 | (2006.01) |

(52) U.S. Cl.
CPC .............. C07K 16/32 (2013.01); A61K 45/06 (2013.01); A61P 35/00 (2018.01); C12Q 1/6886 (2013.01); G01N 33/5005 (2013.01); G01N 33/57407 (2013.01); G01N 33/57415 (2013.01); G01N 33/57484 (2013.01); G01N 33/6893 (2013.01); G01N 33/74 (2013.01); A61K 2039/505 (2013.01); C07K 2317/30 (2013.01); C07K 2317/34 (2013.01); C07K 2317/73 (2013.01); C12Q 2600/112 (2013.01); C12Q 2600/158 (2013.01); G01N 2333/71 (2013.01); G01N 2800/52 (2013.01)

(58) Field of Classification Search
CPC combination set(s) only.
See application file for complete search history.

(56) References Cited

U.S. PATENT DOCUMENTS

| | | | | |
|---|---|---|---|---|
| 7,829,297 B2* | 11/2010 | Spector | ............ | G01N 33/57492 435/7.1 |
| 8,349,574 B2* | 1/2013 | Bates | ..................... | C07K 16/32 435/7.23 |

(Continued)

FOREIGN PATENT DOCUMENTS

| | | |
|---|---|---|
| JP | 2002530629 | 9/2002 |
| JP | 2008530123 | 8/2008 |

(Continued)

OTHER PUBLICATIONS

Sperinde et al (Clinical Cancer Research, 2010, 16:4226-4235).*

(Continued)

*Primary Examiner* — Laura B Goddard

(74) *Attorney, Agent, or Firm* — Kilpatrick Townsend & Stockton LLP

(57) ABSTRACT

The present invention relates generally to methods of accurately quantifying HER2 and/or p95 expression in subjects with a HER2 positive cancer and indicating the risk of brain relapse in such patients.

11 Claims, 7 Drawing Sheets

(56) References Cited

U.S. PATENT DOCUMENTS

| | | | |
|---|---|---|---|
| 8,470,542 B2* | 6/2013 | Sperinde | C12Q 1/6886 |
| | | | 435/7.1 |
| 9,766,242 B2* | 9/2017 | Bates | C07K 16/28 |
| 2006/0204966 A1* | 9/2006 | Spector | A61P 35/00 |
| | | | 435/6.14 |
| 2010/0143927 A1 | 6/2010 | Sperinde et al. | |

FOREIGN PATENT DOCUMENTS

| | | |
|---|---|---|
| JP | 6626037 | 12/2019 |
| WO | 2010083463 | 7/2010 |
| WO | 2010083470 | 7/2010 |
| WO | 2010132723 | 11/2010 |
| WO | 2011008990 | 1/2011 |

OTHER PUBLICATIONS

Scaltriti et al (Clinical Cancer Research, May 1, 2010; 16:2688-2695).*
Esteva et al (Nature Reviews Clinical Oncology, Feb. 2010, 7:98-107).*
Harbeck et al (Breast Care, 2008, 3(suppl 1):7-12).*
Margolese et al (Editors Kufe DW, Pollock RE, Weichselbaum RR, et al. Holland-Frei Cancer Medicine. 6th edition. Hamilton (ON): BC Decker; 2003; "Management of Metastatic Breast Cancer," internet pp. 1-14).*
Science Daily, May 9, 2010, p. 1-2.*
Saez et al (Clinical Cancer Research, 2006, 12:424-431).*
Scaltriti et al (J National Cancer Institute, 2007, 99:628-638).*
CA2,835,284 , "Office Action", dated Jun. 10, 2019, 6 pages.
Church et al., "Her2-positive Breast Cancer Brain Metastases: Multiple Responses to Systemic Chemotherapy and Trastuzumab—A Case Report", Journal of Neuro-Oncology, vol. 79, No. 3, Sep. 2006, pp. 289-292.
JP2017-93074 , "Office Action", dated Mar. 27, 2019, 10 pages.
Niwinska et al., "Occult Brain Metastases in Her2-positive Breast Cancer Patients: Frequency and Response to Radiotherapy", Acta Oneal, vol. 46, No. 7, 2007, pp. 1027-1029.
Niwinska et al., "The Effect of Early Detection of Occult Brain Metastases in Her2-Positive Breast Cancer Patients on Survival and Cause of Death", International Journal of Radiation Oncology Biology Physics, vol. 77, No. 4, Jul. 15, 2010, pp. 1134-1139.
Ono et al., "Brain Metastases in Patients Who Receive Trastuzumab-Containing Chemotherapy for Her2-overexpressing Metastatic Breast Cancer", International Journal of Clinical Oncology, vol. 14, Issue 1, Feb. 2009, pp. 48-52.
CA2,835,284 , "Notice of Allowance", dated Apr. 15, 2020, 1 page.
U.S. Appl. No. 16/166,816, Non-Final Office Action, dated Nov. 2, 2020, 19 pages.
Bendell, J. et al., "Central Nervous System Metastases in Women Who Receive Trastuzumab-Based Therapy for Metastatic Breast Carcinoma", Cancer, 97(12):2972-2977 (2003).
Clayton, A. J. et al., "Incidence of Cerebral Metastases in Patients Treated with Trastuzumab for Metastatic Breast Cancer", British Journal of Cancer, 91(4):639-643 (2004).
Stemmler, H.J. et al., "Characteristics of Patients with Brain Metastases Receiving Trastuzumab for HER2 Overexpressing Metastatic Breast Cancer", The Breast, 15(2):219-225 (2006).

* cited by examiner

A.

B.

METHODS FOR DETERMINING THE LIKELIHOOD OF SURVIVAL AND FOR PREDICTING LIKELIHOOD OF METASTASIS IN CANCER PATIENTS

CROSS-REFERENCE TO RELATED APPLICATIONS

This application is a continuation-in-part application of U.S. patent application Ser. No. 13/476,735, filed May 21, 2012, which claims the benefit of and priority under 35 U.S.C. § 119(e) to U.S. Provisional Patent Application Ser. No. 61/488,028, filed May 19, 2011. These applications are each incorporated herein by reference in their entireties.

This application is a continuation-in-part application of U.S. patent application Ser. No. 14/737,742, filed Jun. 12, 2015, which is a continuation of U.S. patent application Ser. No. 13/911,329, filed Jun. 6, 2013, and issued as U.S. Pat. No. 9,081,019 on Jul. 14, 2015, which is a divisional of U.S. patent application Ser. No. 12/629,037, filed Dec. 1, 2009, and issued as U.S. Pat. No. 8,470,542 on Jun. 25, 2013, which claims the benefit of and priority under 35 U.S.C. § 119(e) to U.S. Provisional Application No. 61/118,975, filed Dec. 1, 2008, U.S. Provisional Application No. 61/182,282, filed May 29, 2009, and U.S. Provisional Application No. 61/187,960, filed Jun. 17, 2009. These applications are each incorporated herein by reference in their entireties.

This application is a continuation-in-part application of U.S. patent application Ser. No. 15/681,895, filed Aug. 21, 2017, which is a continuation of U.S. patent application Ser. No. 14/802,170, filed Jul. 17, 2015, and issued as U.S. Pat. No. 9,766,242 on Sep. 19, 2017, which is a continuation of U.S. patent application Ser. No. 13/670,508, filed Nov. 7, 2012, and issued as U.S. Pat. No. 9,110,066 on Aug. 18, 2015, which is a divisional application of U.S. patent application Ser. No. 12/688,798, filed Jan. 15, 2010, and issued as U.S. Pat. No. 8,349,574 on Jan. 8, 2013, which claims the benefit of and priority under 35 U.S.C. § 119(e) to U.S. Provisional Application No. 61/176,630, filed May 8, 2009, U.S. Provisional Application No. 61/187,962, filed Jun. 17, 2009, and U.S. Provisional Application No. 61/145,029, filed Jan. 15, 2009. These applications are each incorporated herein by reference in their entireties.

FIELD

The present invention relates generally to methods of accurately quantifying total HER2 or p95 expression in patients with a HER2 positive cancer, such as advanced breast cancer, and correlating HER2 or p95 expression with the risk of brain relapse in such patients.

BACKGROUND

Brain metastases accompanying breast cancer are associated with particularly poor prognosis. Brain metastases seriously affect quality of life and are relatively resistant to systemic therapies. Breast cancer is the second most common cause of brain metastases. Though the biological basis is not yet fully understood, patients with HER2-positive breast cancer are at a particularly high risk of brain metastases. However, currently there are no clinical or biological features that have been shown to consistently associate with a propensity to develop brain relapse in HER2-positive advanced breast cancer patients. Similarly, no robust molecular marker to predict brain relapse has been developed.

Current methodologies for determining of HER2 status include immunohistochemistry (IHC) to detect HER2 protein overexpression, fluorescence in situ hybridization (FISH), or chromogenic in situ hybridization to detect amplification of the HER2 gene. However, considerable controversy still exists regarding the accuracy, reliability, and inter-observer variability of these assay methods. For example, the assessment of HER2 expression by IHC is inherently subjective and semi-quantitative (scored as 0, 1+, 2+, 3+). The FISH test, where HER2 gene copy number is counted, is more quantitative analytically, but multiple clinical studies have failed to demonstrate a relationship between HER2 gene copy number and response to clinical treatment. Using currently available techniques, it is estimated that approximately 20% of HER2 testing may be inaccurate.

Currently, the standard component of systemic therapy in HER2-positive breast cancer patients is trastuzumab, a monoclonal antibody against the extracellular domain of the HER2 receptor. However, due to a high molecular weight (approx. 145,000 Da), and physical and chemical properties, trastuzumab does not cross the blood-brain barrier and is ineffective in preventing and treating brain metastases. In addition, a subgroup of HER2-overexpressing tumors also have p95 HER2 (p95), an N-terminal truncated version of HER2 that has shed the ectodomain. As trastuzumab binds to the ectodomain of HER2, it cannot bind the p95 truncated HER2 protein, so trastuzumab is ineffective in patients with high levels of p95.

Because cancer is such a complex disease, many new targeted therapies, while extremely effective in some individual patients, have limited effectiveness in the general patient population for a particular cancer. Without appropriate knowledge about the patient, healthcare providers may be unable to select an effective targeted therapy for the patient. For example, some patients with advanced breast cancer may be at an increased risk of brain metastasis, but the treatment that they are receiving may be inappropriate for preventing or treating brain metastasis.

Therefore, what is needed is a method for accurately quantifying total HER2 or p95 expression and a method to correlate HER2 or p95 level with the risk of brain relapse in patients with advanced breast cancer. What are also needed are methods for identifying therapeutic treatment strategies that are specifically tailored to the subpopulation of HER2-positive advanced breast cancer patients. Methods for selecting a course of treatment for an individual with a HER2-positive cancer and for monitoring the progress of a course of treatment are also needed.

SUMMARY

The present invention relates generally to methods of accurately quantifying total HER2 or p95 expression in patients with advanced breast cancer and correlating HER2 or p95 expression with the risk of brain relapse and time to brain metastasis (TTBM) in such patients. Embodiments of the invention described herein include methods that utilize VeraTag® technology to accurately quantify total HER2 and p95 protein expression in tumor samples and correlate HER2 level and the risk of brain relapse in HER2-positive advanced breast cancer patients, including patients that received treatment, such as trastuzumab.

Embodiments of the invention include a novel assay that precisely quantifies total HER2 expression (H2T), p95 and HER2 homodimers (H2D) in biological samples.

BRIEF DESCRIPTION OF THE FIGURES

Non-limiting embodiments of the methods and systems of the invention are exemplified in the following figures.

DETAILED DESCRIPTION

Definitions and Abbreviations

Figure 1:
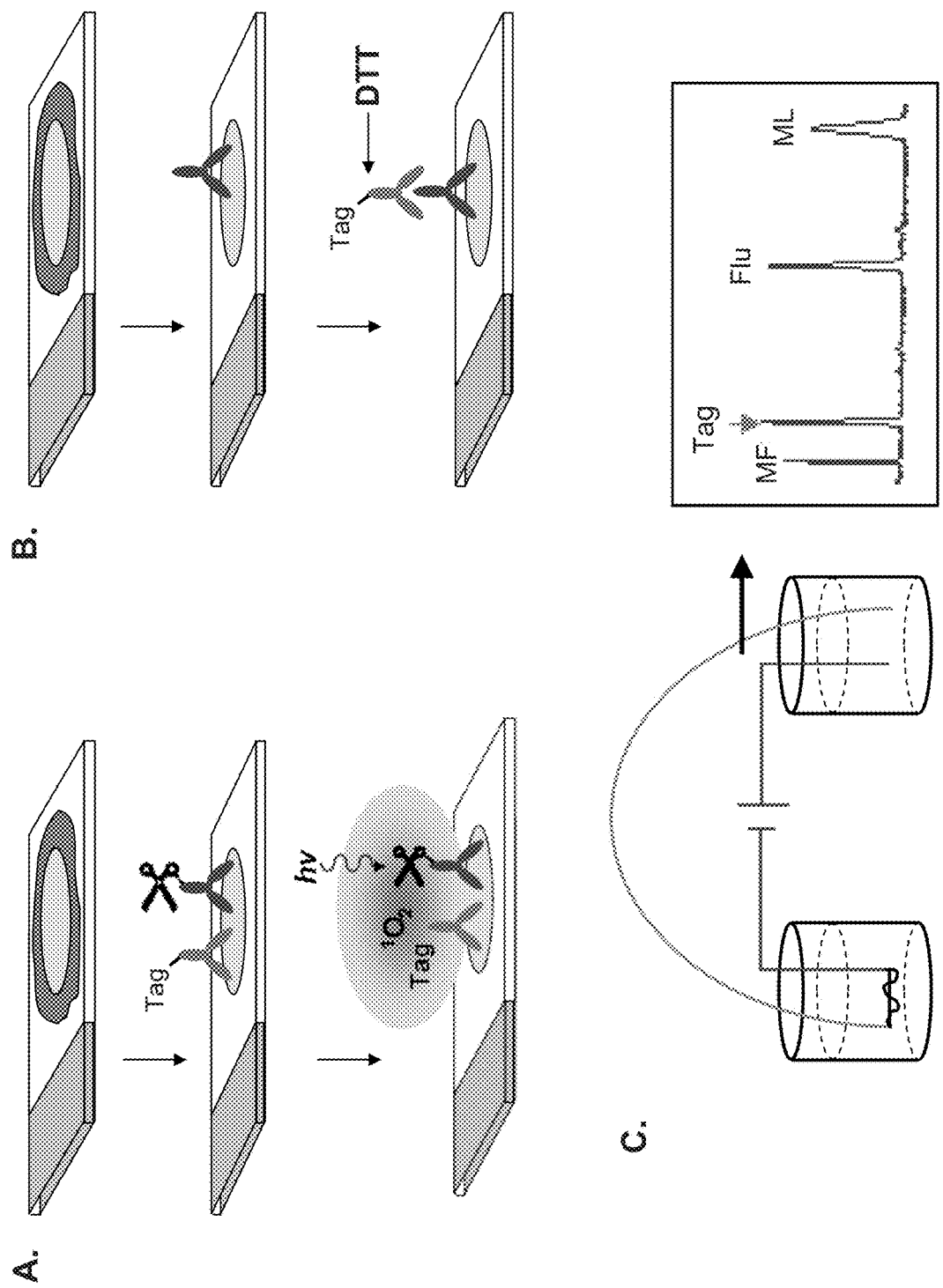
FIG. 1 shows two exemplary assay formats based on VeraTag® technology according to embodiments of the invention. Panel A depicts a standard HerMark® assay format, which is a proximity-based assay where cleavage of the VTag® reporter molecule occurs via singlet oxygen. The symbol of the scissors represents the cleavage moiety attached to the cleavage agent, while "hv" represent light energy. In Panel B, cleavage of the VTag® reporter molecule is effected by a reducing agent (e.g., DTT). In both assay formats, released VTag® reporter molecules are separated and identified by capillary electrophoresis. The x-axis shows the time at which the cleaved VTag® reporter molecule eluted from the capillary, and the fluorescence intensity is shown on the y-axis. Peaks denote the elution of different VTag® reporter molecules.

As used herein, the terms "embodiment" and "aspect" are used interchangeably.

The term "about," as used herein, unless otherwise indicated, refers to a value that is not more than 10% above or below the value being modified by the term. For example, the term "about 5 µg/kg" means a range of from 4.5 µg/kg to 5.5 µg/kg. As another example, "about 1 hour" means a range of from 48 minutes to 72 minutes.

"Antibody" means an immunoglobulin that specifically binds to, and is thereby defined as complementary with, a particular spatial and polar organization of another molecule. The antibody can be monoclonal, polyclonal, or recombinant and can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b, IgG3, IgM, etc. Fragments thereof may include Fab, Fv, and F(ab')$_2$, Fab', and the like. Antibodies may also be single-chain antibodies or an antigen-binding fragment thereof, chimeric antibodies, humanized antibodies or any other antibody derivative known to one of skill in the art that retains binding activity that is specific for a particular binding site. In addition, aggregates, polymers, and conjugates of immunoglobulins or their fragments can be used where appropriate so long as binding affinity for a particular binding site is maintained. Guidance in the production and selection of antibodies and antibody derivatives for use in immunoassays, including such assays employing releasable molecular tag (as described below) can be found in readily available texts and manuals, e.g., Harlow and Lane, 1988, *Antibodies: A Laboratory Manual*, Cold Spring Harbor Laboratory Press, New York; Howard and Bethell, 2001, *Basic Methods in Antibody Production and Characterization*, CRC Press; Wild, ed., 1994, *The Immunoassay Handbook*, Stockton Press, New York.

"Antibody binding composition" means a molecule or a complex of molecules that comprises one or more antibodies, or antigen-binding fragments that bind to a molecule, and derives its binding specificity from such antibody or antibody-binding fragment. Antibody binding compositions include, but are not limited to, (i) antibody pairs in which a first antibody binds specifically to a target molecule and a second antibody binds specifically to a constant region of the first antibody; a biotinylated antibody that binds specifically to a target molecule and a streptavidin protein, which protein is derivatized with moieties such as molecular tags or photosensitizers or the like, via a biotin moiety; (ii) antibodies specific for a target molecule and conjugated to a polymer, such as dextran, which, in turn, is derivatized with moieties such as molecular tags or photosensitizers, either directly by covalent bonds or indirectly via streptavidin-biotin linkages; (iii) antibodies specific for a target molecule and conjugated to a bead, or microbead, or other solid phase support, which, in turn, is derivatized either directly or indirectly with moieties such as molecular tags or photosensitizers, or polymers containing the latter.

"Antigenic determinant," or "epitope" means a site on the surface of a molecule, usually a protein, to which a single antibody molecule binds. Generally, a protein has several or many different antigenic determinants and reacts with antibodies of different specificities. A preferred antigenic determinant is a phosphorylation site of a protein.

"Binding compound" shall refer to an antibody binding composition, an antibody, a peptide, a peptide or non-peptide ligand for a cell surface receptor, a protein, an oligonucleotide, an oligonucleotide analog, such as a peptide nucleic acid, a lectin, or any other molecular entity that is capable of specifically binding to a target protein or molecule or stable complex formation with an analyte of interest, such as a complex of proteins. In one aspect, a binding compound, which can be represented by the formula below, comprises one or more molecular tags attached to a binding moiety.

As used herein, the "blood-brain barrier" refers to a separation of circulating blood from the brain extracellular fluid (BECF) in the central nervous system (CNS). The blood brain barrier is both a physical barrier and a system of cellular transport mechanisms. Endothelial cells restrict the diffusion of microscopic objects (e.g., bacteria) and large or hydrophilic molecules into the cerebrospinal fluid, while allowing the diffusion of small hydrophobic molecules.

"Binding moiety" means any molecule to which molecular tags can be directly or indirectly attached that is capable of specifically binding to an analyte. Binding moieties include, but are not limited to, antibodies, antibody binding compositions, antibody fragments, peptides, and proteins. Preferably, binding moieties are antibodies or antibody binding compositions.

"Cancer" and "cancerous" refer to or describe the physiological condition in an organism, such as a mammal, that is typically characterized by unregulated cell growth. Examples of cancer include, but are not limited to, carcinoma, lymphoma, blastoma, sarcoma and leukemia. More particular examples of such cancers include squamous cell cancer, lung cancer, e.g., small-cell lung cancer or non-small cell lung cancer; gastrointestinal cancer, pancreatic cancer, glioblastoma, cervical cancer, ovarian cancer, liver cancer, bladder cancer, hepatoma, breast cancer, colon cancer, colorectal cancer, endometrial carcinoma, salivary gland carcinoma, kidney cancer, prostate cancer, vulval cancer, thyroid cancer, hepatic carcinoma, and various types of head and neck cancer.

"Chemotherapeutic agent" means a chemical substance, primarily a cytotoxic or cytostatic agent, that is used to treat a condition, particularly cancer. Chemotherapeutic agents shall include such compounds as paclitaxel, as set forth herein.

A "cleavable linkage," as used herein, refers to a chemical linking group that may be cleaved under conditions that do not degrade the structure or affect detection characteristics of a molecular tag connected to a binding moiety with the cleavable linkage.

A "cleavage-inducing moiety," or "cleaving agent," as used herein, is a group that produces an active species that is capable of cleaving a cleavable linkage, for example by oxidation. Preferably, the active species is a chemical species that exhibits short-lived activity so that its cleavage-inducing effects are only in the proximity of the site of its generation.

A "cleaving probe," as used herein, refers to a reagent that comprises a cleavage-inducing moiety as defined herein and an antibody binding composition, an antibody, an antibody fragment, a peptide or non-peptide ligand for a cell surface receptor, or a protein, such as biotin or streptavidin, an oligonucleotide, a lectin or any other molecular entity that is capable of specifically binding to a target protein or molecule or stable complex formation with an analyte of interest (e.g., protein or protein complex).

As used herein, "cutoff" refers to a mathematically determined point based on the measurement of the amount of HER2 or p95 protein in biological samples that can divide samples in a subject population into two distinct patient subgroups, such as, e.g., a median or an optimal or predetermined cutoff. The amount can be measured by any method known in the art such as Fluorescence resonance energy transfer (FRET), Biolumenescent resonance energy transfer (BRET), proximity ligation assay (PLA), dimer-specific antibodies, or VeraTag® assay, or any other method that is well known to one skilled in the art.

"VeraTag® assay" and "VERATAG® assay" are used interchangeably and refer to single and multiplexed and multi-label assays, materials, methods and techniques for performing and utilizing such assays, including but not limited to reagents, analytical procedures and software related to those assays. Such assays are disclosed in this application as well as in U.S. Pat. No. 7,105,308 and in U.S. Patent Publication Nos. 2009/0191559, 2010/0143927, 2010/0210034, and 2010/0233732, which is incorporated by reference herein including any drawings.

As used herein, "VeraTag® reporter molecule" or "vTag," or "vTag®," are used to refer to a molecular tag that is attached to an antibody used in a VeraTag® assay.

As used herein, "greater than or equal to" (i.e., ≥ or >=) can in certain alternative embodiments mean greater than (>). Also, as used herein, "less than or equal to" (i.e., ≤ or <=) can in certain alternative embodiments mean less than (<).

"FFPE" shall refer to a group of cells or quantity of tissue that are fixed, particularly conventional formalin-fixed paraffin-embedded samples. Such samples are typically, without limitation, used in an assay for receptor complexes in the form of thin sections, e.g. 3-10 µm thick, of fixed tissue mounted on a microscope slide or equivalent surface. Such samples also typically undergo a conventional re-hydration procedure, and optionally, an antigen retrieval procedure as a part of, or preliminary to, assay measurements.

"Hazard ratio" or "HR", as used herein, refers to a specific type of relative risk that is calculated using a statistical technique known as Survival Analysis (e.g., analysis of one or more subject groups that have different times to some event or outcome of interest). Survival analysis keeps track of how many subjects have not experienced the event at a given time or during a given time interval. The data is then plotted over the entire time of the study, and the results are graphed as a decreasing curve. "Hazard ratio" is the ratio between the predicted hazard of one group versus another group. The hazard ratio can then be compared to an independent measure (e.g., the amount of one or more biomarkers present in the sample; tumor grade). A hazard ratio greater than one indicates that event of interest is happening faster for a first group than for a second group. A hazard ratio less than one indicates that the event of interest is happening slower for the first group than for the second group. If the HR is indistinguishable from one, there is no statistical difference between the risk associated with the two variables. Note that these ratios are comparisons between the two groups and give no indication of how long it takes for the average subject in either group. The hazard ratio refers to the fold increased or decreased risk of the event of interest in the first group compared to the second group.

"Her-2," "ErbB2," "c-Erb-B2," "HER2," "Her2," and "neu" are used interchangeably herein and refer to native HER2, and allelic variants thereof, as described, for example, in Semba et al., 1985, *P.N.A.S. USA* 82:6497-650 and Yamamoto et al., 1986, *Nature* 319:230-234 and Genebank accession number X03363. Unless indicated otherwise, the terms "HER2," "ErbB2," "c-Erb-B2," "HER2," and "Her2" when used herein refer to the human protein. The gene encoding Her2 is referred to herein as "erbB2." As used herein, H2T shall refer to total HER2 expression as determined, for example without limitation, by VeraTag® assay.

"HER2-acting agent," as used herein, refers to a compound that can inhibit a biological activity of HER2 or a HER2 expressing cell or a HER2 positive cancer cell. Such biological activities include, but are not limited to, dimerization, autophosphorylation, phosphorylation of another receptor, signal transduction, and the like. Biological activities can include, without limitation, cell survival and cell proliferation, and inhibition of such activities by a HER2 acting agent could be direct or indirect cell killing (e.g., ADCC), disruption of protein complexes or complex formation, modulation of protein trafficking, enzyme inhibition or down regulation of HER2. Biological activities can also include patient response as set forth in this application. Exemplary HER2-acting agents include, but are not limited to, the antibodies pertuzumab, ertumaxomab, and trastuzumab and small molecules such as 17-AAG, IPI-504, neratinib, AZD8931, ARRY-380, PF299, afatinib, pelitinib, S-222611, AEE-788 and lapatinib. Antibodies and related molecules are generally too large to pass through the blood-brain barrier.

"HER2 homodimer" in reference to cell surface HER2 membrane receptors means a complex of two or more membrane-bound HER2 proteins. Dimers usually consist of two receptors in contact with one another. Dimers may be created in a cell surface membrane by passive processes, such as Van der Waal interactions, and the like, or dimers may be created by active processes, such as by ligand-induced dimerization, covalent linkages, interaction with intracellular components or the like. See, e.g., Schlessinger, 2000, *Cell* 103:211-225. As used herein, the term "dimer" is understood to refer to "cell surface membrane receptor dimer," unless understood otherwise from the context. As used herein, "H2D" shall refer to quantified dimer as determined, for example without limitation, by VeraTag® assay.

A "HER2 positive" cancer, cancer cell, subject or patient, as used herein, refers to a cancer, cancer cell, subject, or patient exhibiting a score of at least 2 when using a HercepTest® (DakoCytomation California Inc., Carpenteria, Calif.) or a cancer, cancer cell, subject, or patient that has been identified as such by FISH, having a centromere 17 corrected HER2 gene copy number greater than 2 (HER2 FISH/CEP17>2; FISH positive). In certain embodiments, the HER2 positive cell exhibits a score of at least 2+ or 3+ using the HercepTest® Immunohistochemistry assay.

"High" refers to a measure that is greater than normal, greater than a standard (e.g., a predetermined measure or a subgroup measure), or that is relatively greater than another subgroup measure. For example, high HER2 refers to a measure of HER2 that is greater than a normal HER2 measure. A normal HER2 measure may be determined according to any method available to one skilled in the art. High HER2 may also refer to a measure that is equal to or greater than a predetermined measure, such as a predetermined cutoff. High HER2 also may refer to a measure of HER2 wherein a high HER2 subgroup has relatively greater levels of HER2 than another subgroup. For example, without limitation, according to the present invention, two distinct patient subgroups can be created by dividing samples around a mathematically determined point, such as, without limitation, a median, thus creating a subgroup whose measure is high (i.e., higher than the median) and another subgroup whose measure is low. HER2 can be measured by any method known to one skilled in the art such as, for example, without limitation, using a VeraTag® assay, or using any standard immunohistochemical (IHC) method such as HercepTest®. As another example, high HER2 can refer to a measure of HER2 that is greater than a normal measure of HER2 in a particular set of samples or patients that are HER2 positive. A normal HER2 measure may be determined according to any method available to one skilled in the art. As another example, high levels of HER2 may also refer to a measure that is greater than a predetermined measure, such as a predetermined cutoff. High HER2 also may refer to a measure of HER2 wherein a high HER2 homodimer subgroup has a relatively higher level of HER2 homodimers than another subgroup. In some circumstances, "high" refers to an amount that is greater than the median measurement in a reference group.

"Likely to," as used herein, refers to an increased probability that an item, object, thing or event will occur.

"Long," as used herein, refers to a time measure that is greater than normal, greater than a standard such as a predetermined measure, or a subgroup measure that is relatively longer than another subgroup measure. For example, with respect to a patient's longevity, a long time progression refers to time progression that is longer than a normal time progression or longer than time to progression as compared to another group. Whether a time progression is long or not may be determined according to any method available to one skilled in the art. Long could include, for example, no progression. In some circumstances, "long" refers to a time that is greater than the median time course required for a significant event to occur in a disease.

"Low" is a term that refers to a measure that is less than normal, less than a standard (e.g., a predetermined measure or a subgroup measure), or that is relatively less than another subgroup measure. For example, low HER2 means a measure of HER2 that is less than a normal HER2 measure in a particular set of samples of patients that is HER2 positive. A normal HER2 measure may be determined according to any method available to one skilled in the art. Low HER2 may also mean a method that is less than a predetermined measure, such as a predetermined cutoff. Low HER2 may also mean a measure wherein a low HER2 subgroup is relatively lower than another subgroup. For example, without limitation, according to the present specification, two distinct patient subgroups can be created by dividing samples around a mathematically determined point, such as, without limitation, a median, thus creating a group whose measure is low (i.e., less than the median) with respect to another group whose measure is high. As another example, low HER2 means a measure of HER2 homodimers that is less than a normal measure of HER2 in a particular set of samples or patients that is HER2 positive. Low HER2 may also mean a measure that is less than a predetermined measure, such as a predetermined cutoff. Low HER2 may also mean a measure wherein a low HER2 subgroup is relatively less than another subgroup.

A "molecular tag," as used herein, refers to a molecule that can be distinguished from other molecules based on one or more physical, chemical, or optical differences among the molecules being separated, including but not limited to, electrophoretic mobility, molecular weight, shape, solubility, pKa, hydrophobicity, charge, charge/mass ratio, polarity, or the like. In one aspect, molecular tags in a plurality or set differ in electrophoretic mobility and optical detection characteristics and can be separated by electrophoresis. In another aspect, molecular tags in a plurality or set may differ in molecular weight, shape, solubility, pKa, hydrophobicity, charge, or polarity and can be separated by normal phase or reverse phase HPLC, ion exchange HPLC, capillary electrochromatography, mass spectroscopy, gas phase chromatography or like technique. As described herein, a VeraTag® reporter molecule is a type of molecular tag "Optimal cutoff" or "optimized cutoff", as used herein, refers to the value of a predetermined measure in subjects exhibiting certain attributes that allow the best discrimination between two categories of an attribute. For example, finding a value for an optimal cutoff that allows one to best discriminate between two categories (e.g., high H2T expression and low H2T expression) for determining, e.g., overall survival (OS). Optimal cutoffs are used to separate the subjects with values lower than or higher than the optimal cutoff to optimize a prediction model (e.g., for example, without limitation, to maximize the specificity of the model, maximize the sensitivity of the model, maximize the difference in outcome, or minimize the p-value from hazard ratio or a difference in response).

"Overall survival" or "OS" refers to a time as measured from the start of treatment to death or censor. Censoring may come from a study end or change in treatment. Overall survival can refer to a probability as, for example, a probability when represented in a Kaplan-Meier plot of being alive at a particular time, that time being the time between the start of the treatment to death or censor.

As used herein, "p95" refers to an N-terminally truncated, C-terminal portion of HER-2. "p95" has also been referred to as "truncated ErbB2 receptor", "p95$^{ErbB2}$", "p95HER2", and more generally as "NH$_2$-terminally truncated HER-2/neu" and "HER2 C-terminal fragments" to reflect the fact that "p95" represents a family of truncated HER2 proteins similar, but not identical in size to that originally identified as having an apparent molecular weight of 95 kiloDaltons. p95 is thought to be produced by at least two distinct mechanisms. p95 may result from the proteolytic cleavage of full-length HER-2. p95 may also result from an alternative translational start downstream from the canonical first methionine including but not limited to M611 and M687.

As used herein, "photosensitizer" refers to a light-adsorbing molecule that when activated by light converts molecular oxygen into singlet oxygen.

"RECIST" shall mean an acronym that stands for "Response Evaluation Criteria in Solid Tumours" and is a set of published rules that define when cancer patients improve ("respond"), stay the same ("stable") or worsen ("progression") during treatments. Response as defined by RECIST criteria have been published, (see, e.g., Therasse, 2000, *J. Natl. Cancer Inst.* 92(3):205-216). RECIST criteria may include other similar published definitions and rule sets. One skilled in the art would understand definitions that go with RECIST criteria, as used herein, such as partial response (PR), complete response (CR), stable disease (SD) and progressive disease (PD).

"Relative fluorescence units" or "RFUs" are used interchangeably and shall refer to the time integral of a particular capillary electrophoresis peak using arbitrary fluorescence units in comparison to a standard. With respect to VeraTag® assay formats, the RFU is proportional to the concentration of VeraTag® reporter molecule injected into capillary electrophoresis with some expected variability introduced by, for example, injection and capillary differences. The readout of VeraTag® assays are generally given in units of relative fluorescence per mm$^2$ tumor (RF/mm$^2$).

"Relative peak area" or "RPA" are used interchangeably and shall refer to the ratio between an RFU of a particular VeraTag® reporter molecule and an RFU of a known internal fluorescence standard of known and constant concentration.

"Responsiveness," to "respond" to treatment, and other forms of this verb, as used herein, refer to the reaction of a subject to treatment with a HER2-acting agent. As an example, a subject responds to treatment with a Her2-acting agent if growth of a tumor in the subject is retarded about 10%, 20%, 30%, 40%, 50%, 60%, 70%, 80%, 90% or more. In another example, a subject responds to treatment with a HER2-acting agent if a tumor in the subject shrinks by about 5%, 10%, 20%, 30%, 40%, 50%, or more as determined by any appropriate measure, (e.g., by mass or volume). In another example, a subject responds to treatment with a Her2-acting agent if the subject experiences a life expectancy extended by about 5%, 10%, 20%, 30%, 40%, 50%, or more beyond the life expectancy predicted if no treatment is administered. In another example, a subject responds to treatment with a HER2-acting agent if the subject has an increased disease-free survival, overall survival or increased time to progression. Several methods may be used to determine if a patient responds to a treatment including the RECIST criteria, as set forth above.

"Sample," "tissue sample," "biological sample," "patient sample," "patient cell or tissue sample," or "specimen" each refer to a collection of similar cells obtained from a tissue of a subject or patient. The source of the tissue sample may be solid tissue as from a fresh, frozen, and/or preserved organ or tissue sample or biopsy or aspirate; blood or any blood constituents; bodily fluids such as cerebral spinal fluid, amniotic fluid, peritoneal fluid or interstitial fluid; or cells from any time in gestation or development of the subject. The tissue sample may contain compounds that are not naturally intermixed with the tissue in nature such as preservatives, anticoagulants, buffers, fixatives, nutrients, antibiotics or the like. Cells may be fixed in a conventional manner, such as in an FFPE manner.

"Short," as used herein, refers to a time measure that is shorter than normal, shorter than a standard such as a predetermined measure or a subgroup measure that is relatively shorter than another subgroup measure. For example, with respect to a patient's longevity, a short time progression refers to time progression that is shorter than a normal time progression. Whether a time progression is short or not may be determined according to any method available to one skilled in the art. In some circumstances, "short" refers to a time that is less than the median time course required for a significant event to occur in a disease.

As used herein, "significant event" shall refer to an event in a patient's disease that is important as determined by one skilled in the art. Examples of significant events include, for example, without limitation, primary diagnosis, death, recurrence, the determination that a patient's disease is metastatic, relapse of a patient's disease or the progression of a patient's disease from any one of the above noted stages to another. A significant event may be any important event used to assess OS, time to progression (TTP) and/or using the RECIST or other response criteria, as determined by one skilled in the art.

As used herein, "small molecule drug" refers to a low molecular weight organic compound which is by definition not a polymer. The term small molecule, especially within the field of pharmacology, is usually restricted to a molecule that also binds with high affinity to a biopolymer such as protein, nucleic acid, or polysaccharide and in addition alters the activity or function of the biopolymer. The upper molecular weight limit for a small molecule is approximately 1000 Daltons which allows for the possibility to rapidly diffuse across cell membranes so that they can reach intracellular sites of action.

As used herein, the terms "subject" and "patient" are used interchangeably. As used herein, the terms "subject" and "subjects" refer to an animal, preferably a mammal including a non-primate (e.g., a cow, pig, horse, donkey, goat, camel, cat, dog, guinea pig, rat, mouse, sheep) and a primate (e.g., a monkey, such as a cynomolgous monkey, gorilla, chimpanzee and a human).

As used herein, "time course" shall refer to the amount of time between an initial event and one or more subsequent events. For example, with respect to a subject' cancer, time course may relate to a patient's disease and may be measured by gauging significant events in the course of the disease, wherein the first event may be diagnosis and the subsequent event may be, e.g., but not limited to, progression to a later stage, relapse, metastasis, surgery, or death.

"Time to progression" or "TTP" refers to a time as measured from the start of the treatment to progression or a cancer or censor. Censoring may come from a study end or from a change in treatment. Time to progression can also be represented as a probability as, for example, in a Kaplan-Meier plot where time to progression may represent the probability of being progression free over a particular time, that time being the time between the start of the treatment to progression or censor.

"Time to brain metastasis" or "TTBM" refers to a time as measured from the start of the treatment to occurrence of brain metastasis or censor. Censoring may come from a study end or from a change in treatment. Time to brain metastasis can also be represented as a probability of brain metastasis, as, for example, in a Kaplein-Meier plot where time to brain metastasis may represent the probability of being brain metastasis free over a particular time, that time being the time between the start of the treatment to brain metastasis or censor. TTBM is a type of TTP, as brain metastasis may be a significant event in the time course of a subject's cancer.

"Treat," "treatment," and other forms of this word refer to the administration of a Her-acting agent and/or a chemotherapeutic agent and/or other cancer treatment to impede growth of a cancer, to cause a cancer to shrink by weight or volume, and/or to extend the expected survival time of the subject and/or time to progression of the tumor, or the like.

"Unlikely to" refers to a decreased probability that an event, item, object, thing or person will occur with respect to a reference.

DETAILED DESCRIPTION OF CERTAIN EMBODIMENTS

The present invention relates generally to methods of accurately quantifying total HER2 or p95 expression in patients with a HER2 positive cancer, such as advanced breast cancer, and correlating HER2 or p95 expression with the risk of brain metastases in such patients. The methods of the invention enable identification of quantitative HER2 and p95 cutoffs to enable classification of subjects into risk subgroups based on the amount of HER2 and/or p95 in biological samples from the subject. The methods of the invention also enable quantitatitve measurement of HER2 and/or p95 characterization of a subject's risk in relation to a subject population as a whole as well.

In certain embodiments, the invention uses clinical data in combination with measurements of biomarkers to predict patient outcome. The clinical data may include overall survival, time to brain metastasis and progression to metastatic disease. For example, the clinical data may include the date of death or the date of the patient's last follow-up appointment. Or, other aspects of clinical data (e.g., time to metastasis, time to remission, development of resistance to a particular therapeutic agent) may be used. In certain embodiments, the clinical data may comprise the date of starting treatment with a particular anti-HER acting agent or a chemotherapeutic agent. In other embodiments, the invention uses clinical data in order to determine a course of therapeutic action or treatment for a patient, particularly a patient that is at high-risk of relapse/metastasis.

One embodiment is a method for determining the relative likelihood of whether a subject with a HER2− positive cancer is at risk for developing brain metastases comprising (a) obtaining a biological sample of a tumor from the subject's cancer; (b) measuring the amount of at least one of HER2 or p95 in the biological sample; (c) determining whether the amount of at least one of HER2 or p95 protein in the subject's sample is above a HER2 cutoff or a p95 cutoff; and (d) indicating that, if the amount of HER2 or p95 protein in the biological sample are above the HER2 cutoff or p95 cutoff, the subject is more likely to be at risk for developing brain metastases.

Still another embodiment is a method for selecting a course of treatment for a subject with a HER2-2 positive cancer comprising obtaining a biological sample of a tumor from the subject's cancer, (a) obtaining a biological sample of a tumor from the subject's cancer; (b) measuring the amount of at least one of HER2 or p95 in the biological sample; (c) determining whether the amount of at least one of HER2 or p95 protein in the subject's sample is above a HER2 cutoff or a p95 cutoff; and (d) indicating an appropriate course of treatment for the subject based on the amount of HER2 or p95 protein in the biological sample are above the HER2 cutoff or p95 cutoff.

In one embodiment, the invention comprises a method of identifying subjects with HER2 positive cancer that should be screened for brain metastasis, comprising: (a) obtaining a biological sample of a tumor from the subject's cancer; (b) measuring the amount of at least one of HER2 or p95 in the biological sample; (c) determining whether the amount of at least one of HER2 or p95 protein in the subject's sample is above a HER2 cutoff or a p95 cutoff; and (d) indicating that the subject should be screened for brain metastasis if the amount of at least one of HER2 or p95 is above the HER2 cutoff or the p95 cutoff.

In another embodiment, the invention comprises a method of identifying subjects with HER2 positive cancer that should receive treatment with a HER2-acting agent and a second form of cancer treatment, comprising: (a) obtaining a biological sample of a tumor from the subject's cancer; (b) measuring the amount of at least one of HER2 or p95 in the biological sample; (c) determining whether the amount of at least one of HER2 or p95 protein in the subject's sample is above a HER2 cutoff or a p95 cutoff; and (d) indicating that the subject should receive treatment with a HER2-acting agent and a second form of cancer treatment if the amount of at least one of HER2 or p95 is above the HER2 cutoff or the p95 cutoff.

In another embodiment, the invention comprises a method for determining an expected time to brain metastasis (TTBM) in a subject with a HER2-positive cancer comprising: (a) obtaining a biological sample of a tumor from the subject's cancer; (b) measuring the amount of at least one of HER2 or p95 in the biological sample; (c) determining whether the amount of at least one of HER2 or p95 protein in the subject's sample is above a HER2 cutoff or a p95 cutoff; and (d) indicating the subject's expected TTBM based on the incidence of brain metastasis over time in a reference population having HER2 or p95 levels above or below the HER2 cutoff or p95 cutoff.

In an embodiment, the invention comprises a method of determining if a subject with HER2 positive cancer is within in a subset of HER2 positive cancer subjects that should be screened for brain metastasis, comprising: (a) obtaining a biological sample of a tumor from the subject's cancer; (b) measuring the amount of at least one of HER2 or p95 in the biological sample; (c) determining whether the amount of at least one of HER2 or p95 protein in the subject's sample is above a HER2 cutoff or a p95 cutoff; and (d) indicating that the subject should be screened for brain metastasis if the amount of at least one of HER2 or p95 is above the HER2 cutoff or the p95 cutoff.

Another embodiment is a method for predicting time to brain metastasis (TTBM) in a subject with a HER2-positive cancer comprising obtaining a biological sample of a tumor from the subject's cancer, (a) obtaining a biological sample of a tumor from the subject's cancer; (b) measuring the amount of at least one of HER2 or p95 in the biological sample; (c) determining whether the amount of at least one of HER2 or p95 protein in the subject's sample is above a HER2 cutoff or a p95 cutoff; and (d) identifying the TTBM based on the amount of HER2 or p95 protein in the biological sample. In some embodiments, if the amount of HER2 in the biological sample is above the HER2 cutoff the subject's chance of being free of brain metastasis is about 73% at about 1 year, about 61% at about 2 years, and about 37% at about 3 years. In some embodiments, if the amount of HER2 in the biological sample is below the HER2 cutoff the subject's chance of being free of brain metastasis is about 89% at about 1 year, about 78% at about 2 years, and about 69% at about 3 years. In certain embodiments, if the amount of p95 in the biological sample is above the p95 cutoff the subject's chance of being free of brain metastasis is about 77% at about 1 year, about 63% at about 2 years, and about 40% at about 3 years. In some embodiments, if the amount of p95 in the biological sample is below the p95 cutoff the subject's chance of being free of brain metastasis is about 85% at about 1 year, about 77% at about 2 years, and about 67% at about 3 years. In certain embodiments, the amount of HER2 in the biological sample is below the HER2 cutoff and the amount of p95 is above the p95 cutoff the subject's chance of being free of brain metastasis is about 80% at about 1 year, about 66% at about 2 years, and about 50% at about 3 years. In certain embodiments, if the amount of HER2 in the biological sample is below the HER2 cutoff and the amount of p95 is below the p95 cutoff the subject's chance of being free of brain metastasis is about 94% at about 1 year, about 86% at about 2 years, and about 80% at about 3 years. In some embodiments, the subject has about a 2.6 fold increased risk of brain metastasis if the amount of HER2 in the biological sample is above the HER2 cutoff as compared to if the amount is below the HER2 cutoff. In certain embodiments, the subject has about a 2 fold increased risk of brain metastasis if the amount of p95 in the biological sample is above the p95 cutoff as compared to if the amount is below the p95 cutoff. In some embodiments, the subject has about a 5.7 fold decreased risk of brain metastasis if the subject's cancer is Grade 1 or 2 and the amount of HER2 in the biological sample is below the HER2 cutoff as compared to if the subject's cancer was Grade 3 or if the subject's cancer was Grade 1 or 2 and the amount of the amount of HER2 in the biological sample is above the HER2 cutoff.

The embodiments set for below are aspects of each of the methods described herein.

In some embodiments, the subject's cancer has been characterized as HER2-positive based on elevated levels of HER2 gene expression, HER2 protein level, or HER2 gene amplification. In some embodiments, the subject's cancer comprises breast cancer. In certain embodiments, the subject's cancer comprises primary breast cancer. In some embodiments, HER2 gene amplification is determined by fluorescence in situ hybridization (FISH). In certain embodiments, the HER2 protein levels are determined by an immunoassay. In certain embodiments, the HER2 protein levels are determined by a VeraTag® assay. In some embodiments, HER2 gene amplification is determined by quantitation of HER2 mRNA levels.

In certain embodiments, the subject has undergone treatment with a HER2 acting agent that does not cross the blood-brain barrier. In some embodiments, the HER2-acting agent is a monoclonal antibody. In some embodiments, the monoclonal antibody is trastuzumab, pertuzumab, ertumaxomab, tratuzumab emtansine and/or MM-111. In some embodiments, the HER2-acting agent comprises a single-chain antibodies, an antibody fragment (e.g., Fab fragment), or a genetically engineered protein that can bind to an antigen (e.g., an Affybody™, an Adnectin™, a mono-body, a modified Fc region fragment, an immuno-adhesin molecule, or other such molecules.

In some embodiments, the second form of cancer treatment comprises a HER2-targeted small molecule drug, chemotherapy and/or radiation therapy. In certain embodiments, the HER2-targeted small molecule drug comprises hydrophobic molecules such as, e.g., lapatinib, neratinib, AZD8931, ARRY-380, PF299, afatinib, pelitinib, S-222611, or AEE-788. In some embodiments, other hydrophobic small molecule drugs are appropriate. In some embodiments, the second form of cancer treatment comprises a small molecule drug that binds to a protein that binds to HER2. For example, in some embodiments, the small molecule drug comprises drugs that bind to HSP90 such as, e.g., 17-AAG or IPI-504.

The methods of the invention enable identification of quantitative HER2 and p95 cutoffs to enable classification of subjects into risk subgroups based on the amount of HER2 and/or p95 in biological samples from the subject. The methods of the invention also enable quantitative measurement of HER2 and/or p95 characterization of a subject's risk in relation to a subject population as a whole as well.

For each of the methods disclosed herein, the method may further comprise the step of determining the HER2 cutoff and/or p95 cutoff. In some embodiments, the HER2 cutoff and/or the p95 cutoff are determined using a VeraTag® assay. In certain embodiments, the HER2 cutoff and/or the p95 cutoff are determined using other methods of quantitation known in the art (e.g., mRNA quantitation, immunoassay, etc. as disclosed herein). In aspects of the invention, if the step of measuring the amount of HER2 protein in the biological sample and the step of determining the HER2 cutoff both comprise use of a VeraTag® assay, the HER2 cutoff comprises a distinct and higher measure than the measure used to characterize the subject's cancer as HER2 positive.

In some embodiments, the HER2 cutoff comprises at least one of: (i) a median amount of HER2 determined in a reference population of subjects with HER2-positive breast cancer, or (ii) an optimized amount of HER2 as determined in a reference population of subjects with HER2-positive breast cancer. In some embodiments, the HER2 cutoff is determined by VeraTag® assay. In certain embodiments, the optimized amount of HER2 (the optimized cutoff) is 50 RF/mm$^2$. In certain embodiments, the HER2 cutoff is 58 RF/mm$^2$. In some embodiments, the p95 cutoff comprises at least one of: (i) a median amount of p95 determined in a reference population of subjects with HER2-positive breast cancer, or (ii) an optimized amount of p95 as determined in a reference population of subjects with HER2-positive breast cancer. In some embodiments, the p95 cutoff is determined by VeraTag® assay. In certain embodiments, the optimized amount of p95 (the optimized cutoff) is 2.8 RF/mm$^2$. In some embodiments, the reference population of subjects with HER2-positive breast cancer have undergone treatment with a HER2-acting agent that does not cross the blood-brain barrier.

In certain embodiments, the amounts of HER2 protein present are determined by contacting a biological sample from a subject with cancer with a binding compound having a molecular tag attached thereto by a cleavable linkage and a cleaving probe having a cleavage inducing-moiety and detecting whether and what molecular tag is released. Some embodiments may be referred to as a HERmark® assay (see e.g., FIGS. 1A and 2A). The HERmark® assay uses two monoclonal antibodies specific for different unique epitopes on the HER2 protein. This enables both antibodies to bind to the same HER2 receptor in close proximity. The fluorescent VeraTag® reporter molecule ("Tag") is conjugated to a monoclonal antibody specific for HER2. A second HER2-specific monoclonal antibody is conjugated to biotin, which is then linked to a photosensitizer molecule (PM). Photoactivation of the sample at a specific wavelength activates the PM, generating singlet oxygen. The singlet oxygen can cleave the VeraTag® reporter in close proximity. See e.g., FIG. 2C. The released VeraTag® reporter is collected and subsequently quantified using standard capillary electrophoresis. The amount of cleaved VeraTag® reporter is proportional to the concentration of HER2 in the sample.

In certain embodiments, the binding compound and the cleaving probe each specifically binds HER2. In certain embodiments, the cleaving probe and the binding probe do not both bind the same epitope. See e.g., FIGS. 1A and 2A. In some embodiments, the cleaving probe and the binding probe both bind the same epitope. See e.g., FIG. 2B. In certain embodiments, if the binding compound is within an effective proximity of the cleavage-inducing moiety of the cleaving probe, the cleavage-inducing moiety cleaves the cleavable linker so that the molecular tag is released. In some embodiments, the amount of HER2 in a sample is determined using a first binding compound specific for HER2 and second binding compound specific for the first binding compound, wherein the second binding compound comprises one or more molecular probes attached thereto. In certain embodiments, the molecular probes are attached via a cleavable linkage. In some embodiments, the cleavable linkage is cleaved by a reducing agent. For example, in some embodiments, the reducing agent comprises dithiothreitol (DTT). See e.g., FIG. 1B. Examples of detection of HER2 by an assay for detection of total HER2 and/or HER2 homodimers is provided in commonly owned U.S. Patent Application Publication Nos. 2009/0191559, 2010/0143927, 2010/0210034, and 2010/0233732, which are incorporated by reference in their entireties herein.

In certain embodiments, the amounts of p95 in a sample are determined using a proximity probe that is capable of binding p95 or an analyte which binds p95 or a p95 complex, the proximity probe having an effective proximity, and having one or more molecular probes attached, wherein binding of the proximity probe and binding compound within the effective proximity produces a signal from the molecular probes that correlates with the presence and/or quantity of p95 or p95 complex. The proximity probe and/or binding compound may further comprise an antibody.

In some embodiments, the amounts of p95 in a sample are determined using a first binding compound specific for p95 but not full length HER2 and second binding compound specific for the first binding compound, wherein the second binding compound comprises one or more molecular probes attached thereto. In certain embodiments, the molecular probes are attached via a cleavable linkage. In some embodiments, the cleavable linkage is cleaved by a reducing agent. For example, in some embodiments, the reducing agent comprises dithiothreitol (DTT). See e.g., FIG. 1B. Examples of detection of p95 is provided in commonly owned U.S. Patent Application Publication Nos. 2010/0143927 and 2010/0210034, now issued as U.S. Pat. Nos. 8,470,542 and 8,349,574, respectively. In certain embodiments, the first binding compound specific for p95 comprises or is one of the antibodies produced by a hybridoma cell lines having accession number PTA-9738 (p95.D3.4), PTA-9739 (p95.D8.2) and PTA-9740 (p95.D9.1), as described in U.S. Patent Application Publication Nos. 2010/0143927 and 2010/0210034, and deposited on Jan. 28, 2009, to the American Type Culture Collection (ATCC, 10801 University 45 Blvd., Manassas, Va.) under conditions prescribed by the Budapest Treaty.

Proximity assays are increasingly useful for the understanding of the biological role of molecular complexes, as well as in the study of biomarkers. For example, binding compounds that specifically bind a target protein can be coupled with many different detection systems to measure the presence and/or quantity of the target protein. Any method known to one of skill in the art to be useful for determining an amount of a target protein can be used in accordance with the present invention. Such methods include but are not limited to Foerster resonance energy transfer (FRET), bioluminescence resonance energy transfer (BRET), biomolecular fluorescence complementation, proximity ligation assay (PLA), scintillation proximity assay (SPA), and immunoassays with target protein specific antibodies, including, e.g., VeraTag® assays, or any other method that is well known to one skilled in the art.

Many advantages are provided by measuring HER2 and p95 using releasable molecular tags, including separation of released molecular tags from an assay mixture providing greatly reduced background and a significant gain in sensitivity and separation and detection providing a convenient multiplexing capability so that multiple receptor complex components may be readily measured simultaneously in the same assay. Assays employing such tags can have a variety of forms and are disclosed in the following references: U.S.

Pat. Nos. 7,105,308; 6,627,400; 7,402,397; 7,402,398 and 7,402,399, as well as International Patent Publication No. WO 2004/011900, each of which is incorporated herein by reference in their entirety. A wide variety of separation techniques may be employed that can distinguish molecules based on one or more physical, chemical or optical differences among molecules being separated including electrophoretic mobility, molecular weight, shape, solubility, pKa, hydrophobicity, charge, charge/mass ratio or polarity. In one embodiment, molecular tags in a plurality or set differ in electrophoretic mobility and optical detection characteristics and are separated by electrophoresis. In another embodiment, molecular tags in a plurality or set may differ in molecular weight, shape, solubility, pKa, hydrophobicity, charge, polarity and are separated by normal phase or reverse phase HPLC, ion exchange HPLC, capillary electrochromatography, mass spectroscopy or gas phase chromatography.

Sets of molecular tags are provided that can be separated into distinct bands or peaks by a separation technique after they are released from binding compounds. Identification and quantification of such peaks provides a measure or profile of the presence and/or amounts of p95. Molecular tags within a set may be chemically diverse; however, for convenience, sets of molecular tags are usually chemically related. For example, they may all be peptides or they may consist of different combinations of the same basic building blocks or monomers or they may be synthesized using the same basic scaffold with different substituent groups for imparting different separation characteristics. The number of molecular tags in a plurality may vary depending on several factors including the mode of separation employed, the labels used on the molecular tags for detection, the sensitivity of the binding moieties and the efficiency with which the cleavable linkages are cleaved.

The invention relates to HER acting agents. For example, a HER2-acting agent can be any such agent known to one of skill in the art. In certain embodiments, the HER2-acting agent is selected from the group consisting of pertuzumab, trastuzumab, ertumaxomab, 17-AAG, IPI-504, neratinib, AZD8931, ARRY-380, PF299, afatinib, pelitinib, S-222611 AEE-788 and lapatinib. In a preferred embodiment, the HER2-acting agent is trastuzumab (Herceptin®). See, e.g., Goldenberg, 1999, *Clin Ther.* 21:309-18; and Shak, 1999, *Semin Oncol.* 26:71-7. Also, other HER2 acting agents may be evaluated using the methods described herein.

Samples containing HER2 and/or HER2 homodimers suitable for use as biomarkers may come from a wide variety of sources, including cell cultures, animal or plant tissues, patient biopsies, or the like. Preferably, samples are human patient samples. Samples are prepared for assays of the invention using conventional techniques, which may depend on the source from which a sample is taken. For biopsies and medical specimens, guidance is provided in the following references: *Theory and Practice of Histological Techniques,* 1977 (Bancroft J D & Stevens A, eds.), Churchill Livingstone, Edinburgh; Pearse, 1980, *Histochemistry. Theory and applied.* 4$^{th}$ ed., Churchill Livingstone, Edinburgh.

In the area of cancerous disease status, examples of patient tissue samples that may be used include, but are not limited to, breast, prostate, ovary, colon, lung, endometrium, stomach, salivary gland, or pancreas. The tissue sample can be obtained by a variety of procedures including surgical excision, aspiration, or biopsy. The tissue may be fresh or frozen. In one embodiment, assays of the invention are carried out on tissue samples that have been fixed and embedded in paraffin and a step of deparaffination is be carried out. A tissue sample may be fixed (i.e., preserved) by conventional methodology. See, e.g., *Manual of Histological Staining Method of the Armed Forces Institute of Pathology,* 1960, 3$^{rd}$ edition (Lee G. Luna, HT (ASCP) ed.), The Blakston Division McGraw-Hill Book Company, New York; *The Armed Forces Institute of Pathology Advanced Laboratory Methods in Histology and Pathology,* 1994 (Ulreka V. Mikel, ed.), Armed Forces Institute of Pathology, American Registry of Pathology, Washington, D.C. One of skill in the art will appreciate that the choice of a fixative is determined by the purpose for which the tissue is to be histologically stained or otherwise analyzed. One of skill in the art will also appreciate that the length of fixation depends upon the size of the tissue sample and the fixative used.

Generally, a tissue sample is first fixed and is then dehydrated through an ascending series of alcohols, infiltrated, and embedded with paraffin or other sectioning media so that the tissue sample may be sectioned. Alternatively, one may section the tissue and fix the sections obtained. By way of example, the tissue sample may be embedded and processed in paraffin by conventional methodology according to conventional techniques described by the references provided above. Examples of paraffin that may be used include, but are not limited to, Paraplast®, Broloid®, and Tissuemay®. Once the tissue sample is embedded, the sample may be sectioned by a microtome according to conventional techniques. Sections may have a thickness in a range from about three microns to about twelve microns, and preferably, a thickness in a range of from about 5 microns to about 10 microns. In one aspect, a section may have a surface area of from about 10 mm$^2$ to about 1 cm$^2$. Once cut, the sections may be attached to slides by several standard methods. Examples of slide adhesives include, but are not limited to, silane, gelatin and poly-L-lysine. Paraffin embedded sections may be attached to positively charged slides and/or slides coated with poly-L-lysine.

If paraffin has been used as the embedding material, the tissue sections are generally deparaffinized and rehydrated to water prior to detection of biomarkers. Tissue sections may be deparaffinized by several conventional standard methodologies. For example, xylenes and a gradually descending series of alcohols may be used according to conventional techniques described by the references provided above. Alternatively, commercially available deparaffinizing non-organic agents such as Hemo-De® (CMS, Houston, Tex.) may be used.

Mammalian tissue culture cells, or fresh or frozen tissues may be prepared by conventional cell lysis techniques (e.g., 0.14 M NaCl, 1.5 mM MgCl$_2$, 10 mM Tris-Cl (pH 8.6), 0.5% Nonidet P-40, and protease and/or phosphatase inhibitors as required). For fresh mammalian tissues, sample preparation may also include a tissue disaggregation step, such as crushing, mincing, grinding or sonication.

Many advantages are provided by measuring dimer populations using releasable molecular tags, including (1) separation of released molecular tags from an assay mixture provides greatly reduced background and a significant gain in sensitivity; and (2) the use of molecular tags that are specially designed for ease of separation and detection provides a convenient multiplexing capability so that multiple receptor complex components may be readily measured simultaneously in the same assay. Assays employing such tags can have a variety of forms and are disclosed in the following references: U.S. Pat. Nos. 6,627,400, 6,673,550, 6,949,347, 7,105,308; published U.S. Patent Application No. and 2009/0191559; and International Patent Publication No. WO 2004/011900, each of which are incorporated herein by reference in their entireties. For example, a wide variety of separation techniques may be employed that can distinguish molecules based on one or more physical, chemical or optical differences among molecules being separated including electrophoretic mobility, molecular weight, shape, solubility, pKa, hydrophobicity, charge, charge/mass ratio, or polarity. In one aspect, molecular tags in a plurality or set differ in electrophoretic mobility and optical detection characteristics and are separated by electrophoresis. In another aspect, molecular tags in a plurality or set may differ in molecular weight, shape, solubility, pKa, hydrophobicity, charge, or polarity and are separated by normal phase or reverse phase HPLC, ion exchange HPLC, capillary electrochromatography, mass spectroscopy, or gas phase chromatography.

Sets of molecular tags are provided that can be separated into distinct bands or peaks by a separation technique after they are released from binding compounds. Identification and quantification of such peaks provides a measure or profile of the presence and/or amounts of receptor dimers. Molecular tags within a set may be chemically diverse; however, for convenience, sets of molecular tags are usually chemically related. For example, they may all be peptides or they may consist of different combinations of the same basic building blocks or monomers or they may be synthesized using the same basic scaffold with different substituent groups for imparting different separation characteristics. The number of molecular tags in a plurality may vary depending on several factors including the mode of separation employed, the labels used on the molecular tags for detection, the sensitivity of the binding moieties and the efficiency with which the cleavable linkages are cleaved.

Measurements made directly on tissue samples may be normalized by including measurements on cellular or tissue targets that are representative of the total cell number in the sample and/or the numbers of particular subtypes of cells in the sample. The additional measurement may be preferred, or even necessary, because of the cellular and tissue heterogeneity in patient samples, particularly tumor samples, which may comprise substantial fractions of normal cells.

As mentioned above, mixtures containing pluralities of different binding compounds may be provided, wherein each different binding compound has one or more molecular tags attached through cleavable linkages. The nature of the binding compound, cleavable linkage and molecular tag may vary widely. A binding compound may comprise an antibody binding composition, an antibody, a peptide, a peptide or non-peptide ligand for a cell surface receptor, a protein, an oligonucleotide, an oligonucleotide analog, such as a peptide nucleic acid, a lectin or any other molecular entity that is capable of specifically binding to a target protein or molecule or stable complex formation with an analyte of interest, such as a HER2 homodimer. In one aspect, a binding compound can be represented by the following formula:

$$B\text{-}(L\text{-}E)_k$$

wherein B is binding moiety; L is a cleavable linkage and E is a molecular tag. In homogeneous assays, cleavable linkage, L, may be an oxidation-labile linkage, and more preferably, it is a linkage that may be cleaved by singlet oxygen. The moiety "-(L-E)$_k$" indicates that a single binding compound may have multiple molecular tags attached via cleavable linkages. In one aspect, k is an integer greater than or equal to one, but in other embodiments, k may be greater than several hundred, e.g. 100 to 500 or k is greater than several hundred to as many as several thousand, e.g. 500 to 5000. Usually each of the plurality of different types of binding compounds has a different molecular tag, E. Cleavable linkages, e.g. oxidation-labile linkages, and molecular tags, E, are attached to B by way of conventional chemistries.

Preferably, B is an antibody binding composition that specifically binds to a target, such as an antigenic determinant on HER2. Antibodies specific for HER2 epitopes are provided in the examples set forth herein. Antibody compositions are readily formed from a wide variety of commercially available antibodies, either monoclonal or polyclonal. In particular, antibodies specific for epidermal growth factor receptors are disclosed in U.S. Pat. Nos. 5,677,171; 5,772,997; 5,968,511; 5,480,968; and 5,811,098, each of which is incorporated by reference in its entirety. U.S. Pat. No. 5,599,681, hereby also incorporated by reference in its entirety, discloses antibodies specific for phosphorylation sites of proteins. Commercial vendors, such as Cell Signaling Technology (Beverly, Mass.), Biosource International (Camarillo, Calif.) and Upstate (Charlottesville, Va.) also provide monoclonal and polyclonal antibodies.

Cleavable linkage, L, can be virtually any chemical linking group that may be cleaved under conditions that do not degrade the structure or affect detection characteristics of the released molecular tag, E. Whenever a cleaving probe is used in a homogeneous assay format, cleavable linkage, L, is cleaved by a cleavage agent generated by the cleaving probe that acts over a short distance so that only cleavable linkages in the immediate proximity of the cleaving probe are cleaved. Typically, such an agent must be activated by making a physical or chemical change to the reaction mixture so that the agent produces a short lived active species that diffuses to a cleavable linkage to effect cleavage. In a homogeneous format, the cleavage agent is preferably attached to a binding moiety, such as an antibody, that targets prior to activation the cleavage agent to a particular site in the proximity of a binding compound with releasable molecular tags. In such embodiments, a cleavage agent is referred to herein as a "cleavage-inducing moiety." An exemplary cleavage linkage is illustrated in FIG. 2C.

In a non-homogeneous format, because specifically bound binding compounds are separated from unbound binding compounds, a wider selection of cleavable linkages and cleavage agents are available for use. Cleavable linkages may not only include linkages that are labile to reaction with a locally acting reactive species, such as hydrogen peroxide, singlet oxygen, or the like, but also linkages that are labile to agents that operate throughout a reaction mixture, such as base-labile linkages, photocleavable linkages, linkages cleavable by reduction, linkages cleaved by oxidation, acid-labile linkages, and peptide linkages cleavable by specific proteases. References describing many such linkages include Greene and Wuts, 1991, *Protective Groups in Organic Synthesis, Second Edition*, John Wiley & Sons, New York; Hermanson, 1996, *Bioconjugate Techniques*, Academic Press, New York; and U.S. Pat. No. 5,565,324.

In one aspect, commercially available cleavable reagent systems may be employed with the invention. For example, a disulfide linkage may be introduced between an antibody binding composition and a molecular tag using a heterofunctional agent such as N-succinimidyl 3-(2-pyridyldithio) propionate (SPDP), succinimidyloxycarbonyl-α-methyl-α-(2-pyridyldithio) toluene (SMPT) or the like, available from vendors such as Pierce Chemical Company (Rockford, Ill.). Disulfide bonds introduced by such linkages can be broken by treatment with a reducing agent, such as dithiothreitol (DTT), dithioerythritol (DTE), 2-mercaptoethanol or sodium borohydride. Typical concentrations of reducing agents to effect cleavage of disulfide bonds are in the range of from 10 to 100 mM. An oxidatively labile linkage may be introduced between an antibody binding composition and a molecular tag using the homobifunctional NHS ester cross-linking reagent, disuccinimidyl tartarate (DST) (available from Pierce) that contains central cis-diols that are susceptible to cleavage with sodium periodate (e.g., 15 mM periodate at physiological pH for 4 hours). Linkages that contain esterified spacer components may be cleaved with strong nucleophilic agents, such as hydroxylamine, e.g., 0.1 N hydroxylamine, pH 8.5, for 3-6 hours at 37° C. Such spacers can be introduced by a homobifunctional cross-linking agent such as ethylene glycol bis(succinimidylsuccinate) (EGS) available from Pierce (Rockford, Ill.). A base labile linkage can be introduced with a sulfone group. Homobifunctional cross-linking agents that can be used to introduce sulfone groups in a cleavable linkage include bis[2-(succinimidyloxycarbonyloxy)ethyl]sulfone (BSOCOES), and 4,4-difluoro-3,3-dinitrophenylsulfone (DFDNPS). Exemplary basic conditions for cleavage include 0.1 M sodium phosphate, adjusted to pH 11.6 by addition of Tris base, containing 6 M urea, 0.1% SDS, and 2 mM DTT, with incubation at 37° C. for 2 hours. Photocleavable linkages also include those disclosed in U.S. Pat. No. 5,986,076.

When L is oxidation labile, L may be a thioether or its selenium analog; or an olefin, which contains carbon-carbon double bonds, wherein cleavage of a double bond to an oxo group, releases the molecular tag, E. Illustrative oxidation labile linkages are disclosed in U.S. Pat. Nos. 5,622,929, 6,627,400 and 6,949,347; each of which is hereby incorporated by reference in their entirety.

Molecular tag, E, in the present invention may comprise an electrophoric tag as described in the following references when separation of pluralities of molecular tags are carried out by gas chromatography or mass spectrometry: See, e.g., Zhang et al., 2002, *Bioconjugate Chem.* 13:1002-1012; Giese, 1983, *Anal. Chem.* 2:165-168; and U.S. Pat. Nos. 4,650,750; 5,360,819; 5,516,931; and 5,602,273, each of which is hereby incorporated by reference in their entirety.

Figure 2:
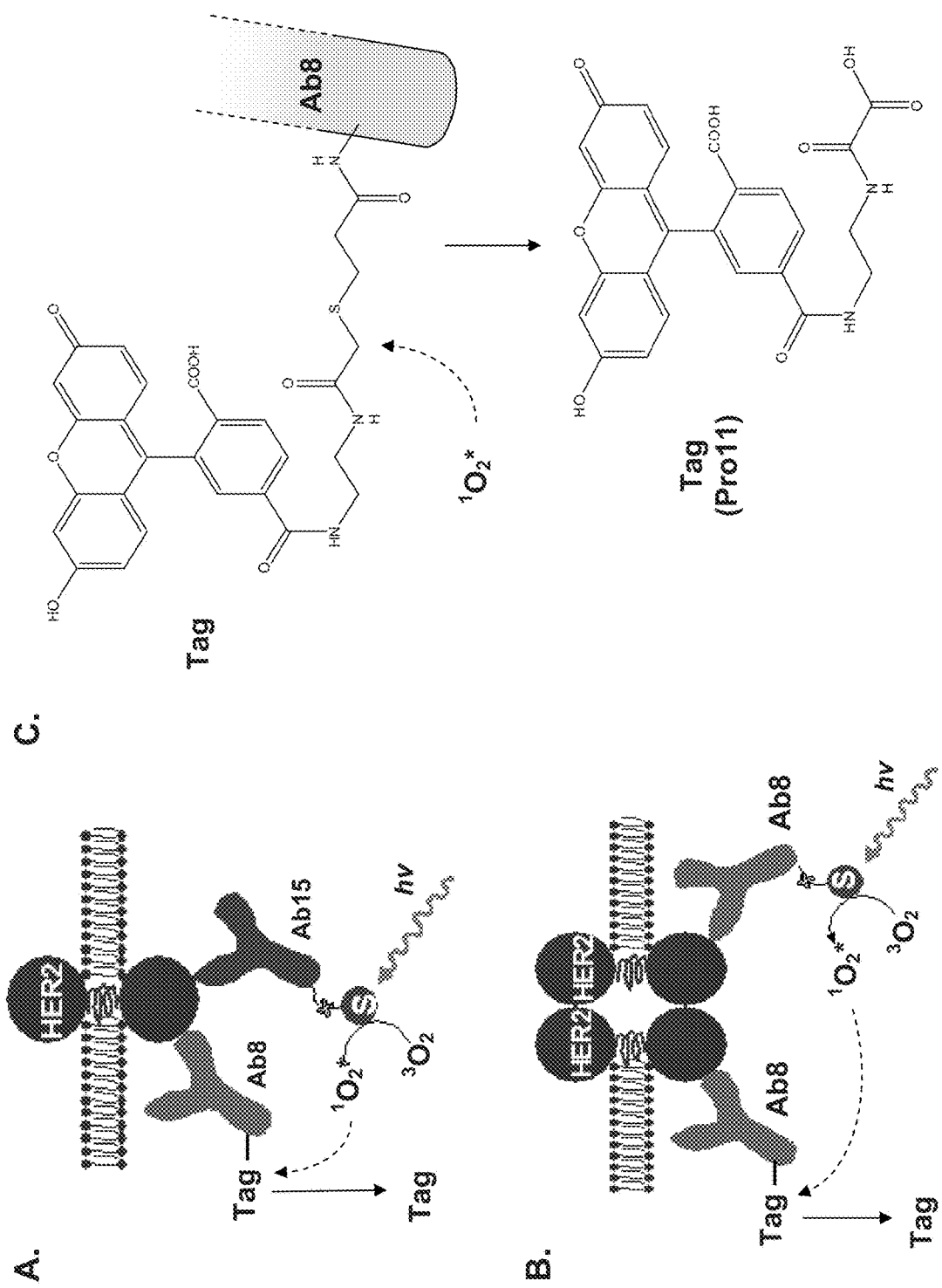
FIG. 2 shows exemplary assay formats based on VeraTag® technology according to embodiments of the invention. Panel A depicts a standard HerMARK® assay format, which enables quantitation of the total amount of target protein (e.g., HER2) using two binding agents (e.g., antibodies) specific for the target protein. Panel B depicts an assay format that enables identification of homodimers using a single antibody that has been differentially conjugated to either a VTag® reporter molecule or a cleaving agent. Both assay formats are proximity-based assays where cleavage of the VTag® reporter molecule occurs via photo-induction of the cleaving agent (i.e., singlet oxygen) by light. "S" represents a streptavidn molecule attached via a biotin molecule to one of the antibodies. Panel C shows an exemplary VTag® reporter molecule (Pro11) attached to an antibody (e.g., Ab8) via a cleavable linker and in released form after cleavage.

Molecular tag, E, is preferably a water-soluble organic compound that is stable with respect to the active species, especially singlet oxygen, and that includes a detection or reporter group. Otherwise, E may vary widely in size and structure. In one aspect, E has a molecular weight in the range of from about 50 to about 2500 daltons, more preferably, from about 50 to about 1500 daltons. E may comprise a detection group for generating an electrochemical, fluorescent or chromogenic signal. In embodiments employing detection by mass, E may not have a separate moiety for detection purposes. Preferably, the detection group generates a fluorescent signal. An exemplary molecular tag (Pro11) is shown in FIG. 2.

Molecular tags within a plurality are selected so that each has a unique separation characteristic and/or a unique optical property with respect to the other members of the same plurality. In one aspect, the chromatographic or electrophoretic separation characteristic is retention time under a set of standard separation conditions conventional in the art, e.g., voltage, column pressure, column type, mobile phase, or electrophoretic separation medium. In another aspect, the optical property is a fluorescence property, such as emission spectrum, fluorescence lifetime, or fluorescence intensity at a given wavelength or band of wavelengths. Preferably, the fluorescence property is fluorescence intensity. For example, each molecular tag of a plurality may have the same fluorescent emission properties, but each will differ from one another by virtue of a unique retention time. On the other hand, one or two or more of the molecular tags of a plurality may have identical migration or retention times, but they will have unique fluorescent properties, e.g. spectrally resolvable emission spectra, so that all the members of the plurality are distinguishable by the combination of molecular separation and fluorescence measurement.

Preferably, released molecular tags are detected by electrophoretic separation and the fluorescence of a detection group. In such embodiments, molecular tags having substantially identical fluorescence properties have different electrophoretic mobilities so that distinct peaks in an electropherogram are formed under separation conditions. Preferably, pluralities of molecular tags of the invention are separated by conventional capillary electrophoresis apparatus, either in the presence or absence of a conventional sieving matrix. During or after electrophoretic separation, the molecular tags are detected or identified by recording fluorescence signals and migration times (or migration distances) of the separated compounds or by constructing a chart of relative fluorescent and order of migration of the molecular tags (e.g., as an electropherogram). Preferably, the presence, absence and/or amounts of molecular tags are measured by using one or more standards as disclosed by published U.S. Patent Application No. 2003/0170734, which is hereby incorporated by reference in its entirety.

Pluralities of molecular tags may also be designed for separation by chromatography based on one or more physical characteristics that include molecular weight, shape, solubility, pKa, hydrophobicity, charge, polarity or the like, e.g. as disclosed in published U.S. Patent Application No. 2003/0235832, which hereby is incorporated by reference in its entirety. A chromatographic separation technique is selected based on parameters such as column type, solid phase, mobile phase and the like, followed by selection of a plurality of molecular tags that may be separated to form distinct peaks or bands in a single operation. Several factors determine which HPLC technique is selected for use in the invention, including the number of molecular tags to be detected (i.e., the size of the plurality), the estimated quantities of each molecular tag that will be generated in the assays, the availability and ease of synthesizing molecular tags that are candidates for a set to be used in multiplexed assays, the detection modality employed and the availability, robustness, cost and ease of operation of HPLC instrumentation, columns and solvents. Generally, columns and techniques are favored that are suitable for analyzing limited amounts of sample and that provide the highest resolution separations. Guidance for making such selections can be found in the literature, such as, for example, Snyder et al., 1988, *Practical HPLC Method Development*, John Wiley & Sons, New York; Millner, 1999, *High Resolution Chromatography: A Practical Approach*, Oxford University Press, New York; Chi-San Wu, 1999, *Column Handbook for Size Exclusion Chromatography*, Academic Press, San Diego; and Oliver, 1989, *HPLC of Macromolecules: A Practical Approach*, Oxford University Press, Oxford, England.

In one aspect, molecular tag, E, is (M, D), where M is a mobility-modifying moiety and D is a detection moiety. The notation "(M, D)" is used to indicate that the ordering of the M and D moieties may be such that either moiety can be adjacent to the cleavable linkage, L. That is, "B-L-(M, D)" designates binding compound of either of two forms: "B-L-M-D" or "B-L-D-M."

Detection moiety, D, may be a fluorescent label or dye, a chromogenic label or dye or an electrochemical label. Preferably, D is a fluorescent dye. Exemplary fluorescent dyes for use with the invention include water-soluble rhodamine dyes, fluoresceins, 4,7-dichlorofluoresceins, benzoxanthene dyes and energy transfer dyes, as disclosed in the following references: *Handbook of Molecular Probes and Research Reagents*, $8^{th}$ ed., 2002, Molecular Probes, Eugene, Oreg.; U.S. Pat. Nos. 4,318,846, 4,997,928, 5,945,526, 6,096,723, 6,191,278, and 6,372,907, and Lee et al., 1997, *Nucleic Acids Research* 25:2816-2822. Preferably, D is a fluorescein or a fluorescein derivative.

Once each of the binding compounds is separately derivatized by a different molecular tag, it is pooled with other binding compounds to form a plurality of binding compounds. Usually, each different kind of binding compound is present in a composition in the same proportion; however, proportions may be varied as a design choice so that one or a subset of particular binding compounds are present in greater or lower proportion depending on the desirability or requirements for a particular embodiment or assay. Factors that may affect such design choices include, but are not limited to, antibody affinity and avidity for a particular target, relative prevalence of a target, fluorescent characteristics of a detection moiety of a molecular tag and the like.

A cleavage-inducing moiety, or cleaving agent, is a group that produces an active species that is capable of cleaving a cleavable linkage, preferably by oxidation. Preferably, the active species is a chemical species that exhibits short-lived activity so that its cleavage-inducing effects are only in the proximity of the site of its generation. Either the active species is inherently short lived, so that it will not create significant background beyond the proximity of its creation, or a scavenger is employed that efficiently scavenges the active species, so that it is not available to react with cleavable linkages beyond a short distance from the site of its generation. Illustrative active species include singlet oxygen, hydrogen peroxide, NADH, and hydroxyl radicals, phenoxy radical, superoxide and the like. Illustrative quenchers for active species that cause oxidation include polyenes, carotenoids, vitamin E, vitamin C, amino acid-pyrrole N-conjugates of tyrosine, histidine and glutathione. See, e.g. Beutner et al., 2000, *Meth. Enzymol.* 319:226-241.

One consideration in designing assays employing a cleavage-inducing moiety and a cleavable linkage is that they not be so far removed from one another when bound to a receptor complex that the active species generated by the cleavage-inducing moiety cannot efficiently cleave the cleavable linkage. In one aspect, cleavable linkages preferably are within about 1000 nm and preferably within about 20-200 nm, of a bound cleavage-inducing moiety. More preferably, for photosensitizer cleavage-inducing moieties generating singlet oxygen, cleavable linkages are within about 20-100 nm of a photosensitizer in a receptor complex. The range within which a cleavage-inducing moiety can effectively cleave a cleavable linkage (that is, cleave enough molecular tag to generate a detectable signal) is referred to herein as its "effective proximity." One of ordinary skill in the art will recognize that the effective proximity of a particular sensitizer may depend on the details of a particular assay design and may be determined or modified by routine experimentation.

A sensitizer is a compound that can be induced to generate a reactive intermediate, or species, usually singlet oxygen. Preferably, a sensitizer used in accordance with the invention is a photosensitizer. Other sensitizers included within the scope of the invention are compounds that on excitation by heat, light, ionizing radiation or chemical activation will release a molecule of singlet oxygen. The best known members of this class of compounds include the endoperoxides such as 1,4-biscarboxyethyl-1,4-naphthalene endoperoxide, 9,10-diphenylanthracene-9,10-endoperoxide and 5,6,11,12-tetraphenyl naphthalene 5,12-endoperoxide. Heating or direct absorption of light by these compounds releases singlet oxygen. Further sensitizers are disclosed by Di Mascio et al., 1994, *FEBS Lett.* 355:287; and Kanofsky, 1983, *J. Biol. Chem.* 258:5991-5993; Pierlot et al., 2000, *Meth. Enzymol.* 319:3-20.

Photosensitizers may be attached directly or indirectly, via covalent or non-covalent linkages, to the binding agent of a class-specific reagent. Guidance for constructing such compositions, particularly for antibodies as binding agents are available in the literature, e.g. in the fields of photodynamic therapy, immunodiagnostics, and the like. Exemplary guidance may be found in Ullman et al., 1994, *Proc. Natl. Acad. Sci. USA* 91, 5426-5430; Strong et al., 1994, *Ann. New York Acad. Sci.* 745: 297-320; Yarmush et al., 1993, *Crit. Rev. Therapeutic Drug Carrier Syst.* 10: 197-252; and U.S. Pat. Nos. 5,340,716, 5,516,636, 5,709,994, and 6,251,581.

A large variety of light sources are available to photoactivate photosensitizers to generate singlet oxygen. Both polychromatic and monochromatic sources may be used as long as the source is sufficiently intense to produce enough singlet oxygen in a practical time duration. The length of the irradiation depends on the nature of the photosensitizer, the nature of the cleavable linkage, the power of the source of irradiation and its distance from the sample. In general, the period for irradiation may be less than about a microsecond to as long as about 10 minutes, usually in the range of about one millisecond to about 60 seconds. The intensity and length of irradiation should be sufficient to excite at least about 0.1% of the photosensitizer molecules, usually at least about 30% of the photosensitizer molecules and preferably, substantially all of the photosensitizer molecules. Exemplary light sources include lasers such as, e.g., helium-neon lasers, argon lasers, YAG lasers, He/Cd lasers and ruby lasers; photodiodes; mercury, sodium and xenon vapor lamps; incandescent lamps such as, e.g., tungsten and tungsten/halogen and flashlamps. An exemplary photoactivation device suitable for use in the methods of the invention is disclosed International Patent Publication No. WO 03/051669. In such embodiments, the photoactivation device is an array of light emitting diodes (LEDs) mounted in housing that permits the simultaneous illumination of all the wells in a 96-well plate.

Examples of photosensitizers that may be utilized in the present invention are those that have the above properties and those disclosed by U.S. Pat. Nos. 5,536,834, 5,763,602, 5,565,552, 5,709,994, 5,340,716, 5,516,636, 6,251,581, and 6,001,673; published European Patent Application No. 0484027; Martin et al., 1990, *Methods Enzymol.* 186:635-645; and Yarmush et al., 1993, *Crit. Rev. Therapeutic Drug Carrier Syst.* 10:197-252. As with sensitizers, in certain embodiments, a photosensitizer may be associated with a solid phase support by being covalently or non-covalently attached to the surface of the support or incorporated into the body of the support. In general, the photosensitizer is associated with the support in an amount necessary to achieve the necessary amount of singlet oxygen. Generally, the amount of photosensitizer is determined empirically according to routine methods.

In one embodiment, a photosensitizer is incorporated into a latex particle to form photosensitizer beads, e.g. as disclosed by U.S. Pat. Nos. 5,709,994 and 6,346,384; and International Patent Publication No. WO 01/84157. Alternatively, photosensitizer beads may be prepared by covalently attaching a photosensitizer, such as rose bengal, to 0.5 micron latex beads by means of chloromethyl groups on the latex to provide an ester linking group, as described in *J. Amer. Chem. Soc.*, 97:3741 (1975). This reaction may be carried out, for example, in a conventional 96-well or 384-well microtiter plate, or the like, having a filter membrane that forms one wall, e.g. the bottom, of the wells that allows reagents to be removed by the application of a vacuum. This allows the convenient exchange of buffers, if the buffer required for specific binding of binding compounds is different than the buffer required for either singlet oxygen generation or separation. For example, in the case of antibody-based binding compounds, a high salt buffer is required. If electrophoretic separation of the released tags is employed, then better performance is achieved by exchanging the buffer for one that has a lower salt concentration suitable for electrophoresis.

As an example, a cleaving probe may comprise a primary haptenated antibody and a secondary anti-hapten binding protein derivatized with multiple photosensitizer molecules. A preferred primary haptenated antibody is a biotinylated antibody and preferred secondary anti-hapten binding proteins may be either an anti-biotin antibody or streptavidin. Other combinations of such primary and secondary reagents are well known in the art. Exemplary combinations of such reagents are taught by Haugland, 2002, *Handbook of Fluorescent Probes and Research Reagents, Ninth Edition*, Molecular Probes, Eugene, Oreg. An exemplary combination of such reagents is described below. There binding compounds having releasable tags ("$mT_1$" and "$mT_2$"), and primary antibody derivatized with biotin are specifically bound to different epitopes of receptor dimer in membrane. Biotin-specific binding protein, e.g. streptavidin, is attached to biotin bringing multiple photosensitizers into effective proximity of binding compounds. Biotin-specific binding protein may also be an anti-biotin antibody and photosensitizers may be attached via free amine group on the protein by conventional coupling chemistries, e.g., Hermanson (supra). An exemplary photosensitizer for such use is an NHS ester of methylene blue prepared as disclosed in published European Patent Application 0510688.

The following general discussion of methods and specific conditions and materials are by way of illustration and not limitation. One of skill in the art will understand how the methods described herein can be adapted to other applications, particularly with using different samples, cell types and target complexes.

In conducting the methods of the invention, a combination of the assay components is made, including the sample being tested, the binding compounds and optionally the cleaving probe. Generally, assay components may be combined in any order. In certain applications, however, the order of addition may be relevant. For example, one may wish to monitor competitive binding, such as in a quantitative assay. Or one may wish to monitor the stability of an assembled complex. In such applications, reactions may be assembled in stages.

The amounts of each reagent can generally be determined empirically. The amount of sample used in an assay will be determined by the predicted number of target complexes present and the means of separation and detection used to monitor the signal of the assay. In general, the amounts of the binding compounds and the cleaving probe can be provided in molar excess relative to the expected amount of the target molecules in the sample, generally at a molar excess of at least about 1.5, more desirably about 10-fold excess, or more. In specific applications, the concentration used may be higher or lower, depending on the affinity of the binding agents and the expected number of target molecules present on a single cell. Where one is determining the effect of a chemical compound on formation of oligomeric cell surface complexes, the compound may be added to the cells prior to, simultaneously with or after addition of the probes, depending on the effect being monitored.

The assay mixture can be combined and incubated under conditions that provide for binding of the probes to the cell surface molecules, usually in an aqueous medium, generally at a physiological pH (comparable to the pH at which the cells are cultures), maintained by a buffer at a concentration in the range of about 10 to 200 mM. Conventional buffers may be used, as well as other conventional additives as necessary, such as salts, growth medium, stabilizers, etc. Physiological and constant temperatures are normally employed. Incubation temperatures normally range from about 4° to 70° C., usually from about 15° to 45° C., more usually about 25° to 37° C.

After assembly of the assay mixture and incubation to allow the probes to bind to cell surface molecules, the mixture can be treated to activate the cleaving agent to cleave the tags from the binding compounds that are within the effective proximity of the cleaving agent, releasing the corresponding tag from the cell surface into solution. The nature of this treatment will depend on the mechanism of action of the cleaving agent. For example, where a photosensitizer is employed as the cleaving agent, activation of cleavage can comprise irradiation of the mixture at the wavelength of light appropriate to the particular sensitizer used.

Following cleavage, the sample can then be analyzed to determine the identity of tags that have been released. Where an assay employing a plurality of binding compounds is employed, separation of the released tags will generally precede their detection. The methods for both separation and detection are determined in the process of designing the tags for the assay. A preferred mode of separation employs electrophoresis, in which the various tags are separated based on known differences in their electrophoretic mobilities.

As mentioned above, in some embodiments, if the assay reaction conditions may interfere with the separation technique employed, it may be necessary to remove, or exchange, the assay reaction buffer prior to cleavage and separation of the molecular tags. For example, assay conditions may include salt concentrations (e.g. required for specific binding) that degrade separation performance when molecular tags are separated on the basis of electrophoretic mobility. Thus, such high salt buffers may be removed, e.g., prior to cleavage of molecular tags, and replaced with another buffer suitable for electrophoretic separation through filtration, aspiration, dilution or other means.

In certain embodiments, the subject may be administered a combination therapy that includes a HER2-acting agent. In some embodiments, the HER2-acting agent may be trastuzumab. The combination therapy can include trastuzumab in combination with one or more of any chemotherapeutic agent known to one of skill in the art without limitation. Preferably, the chemotherapeutic agent has a different mechanism of action from trastuzumab. For example, the chemotherapeutic agent can be an anti-metabolite (e.g., 5-flourouricil (5-FU), methotrexate (MTX), fludarabine, etc.), an antimicrotubule agent (e.g., vincristine; vinblastine; taxanes such as paclitaxel and docetaxel; etc.), an alkylating agent (e.g., cyclophosphamide, melphalan, bischloroethylnitrosurea, etc.), platinum agents (e.g., cisplatin, carboplatin, oxaliplatin, JM-216, CI-973, etc.), anthracyclines (e.g., doxorubicin, daunorubicin, etc.), antibiotic agents (e.g., mitomycin-C, actinomycin D, etc.), topoisomerase inhibitors (e.g., etoposide, camptothecins, etc.) or other any other chemotherapeutic agents known to one skilled in the art.

Particular examples of chemotherapeutic agents that can be used in the various embodiments of the invention, including pharmaceutical compositions, dosage forms, and kits of the invention, include, without limitation, cytarabine, melphalan, topotecan, fludarabine, etoposide, idarubicin, daunorubicin, mitoxantrone, cisplatin paclitaxel, and cyclophosphamide.

Other chemotherapeutic agents that may be used include abarelix, aldesleukin, alemtuzumab, alitretinoin, allopurinol, altretamine, amifostine, anastrozole, arsenic trioxide, asparaginase, BCG live, bevaceizumab, bexarotene, bleomycin, bortezomib, busulfan, calusterone, camptothecin, capecitabine, carboplatin, carmustine, celecoxib, cetuximab, chlorambucil, cinacalcet, cisplatin, cladribine, cyclophosphamide, cytarabine, dacarbazine, dactinomycin, darbepoetin alfa, daunorubicin, denileukin diftitox, dexrazoxane, docetaxel, doxorubicin, dromostanolone, Elliott's B solution, epirubicin, epoetin alfa, estramustine, etoposide, exemestane, filgrastim, floxuridine, fludarabine, fluorouracil, fulvestrant, gemcitabine, gemtuzumab ozogamicin, gefitinib, goserelin, hydroxyurea, ibritumomab tiuxetan, idarubicin, ifosfamide, imatinib, interferon alfa-2a, interferon alfa-2b, irinotecan, letrozole, leucovorin, levamisole, lomustine, meclorethamine, megestrol, melphalan, mercaptopurine, mesna, methotrexate, methoxsalen, methylprednisolone, mitomycin C, mitotane, mitoxantrone, nandrolone, nofetumomab, oblimersen, oprelvekin, oxaliplatin, paclitaxel, pamidronate, pegademase, pegaspargase, pegfilgrastim, pemetrexed, pentostatin, pipobroman, plicamycin, polifeprosan, porfimer, procarbazine, quinacrine, rasburicase, rituximab, sargramostim, streptozocin, talc, tamoxifen, tarceva, temozolomide, teniposide, testolactone, thioguanine, thiotepa, topotecan, toremifene, tositumomab, trastuzumab, tretinoin, uracil mustard, valrubicin, vinblastine, vincristine, vinorelbine, and zoledronate.

In certain embodiments, the biological sample comprises FFPEs. In certain embodiments, the subject's cancer is breast cancer. In certain embodiments, the breast cancer is metastatic. In some embodiments, the breast cancer is early stage breast cancer. In some embodiments, any cancer that may be sensitive to a HER2 acting agent may be monitored. The HER2 acting agent may be any HER2 acting agent. In certain embodiments, the HER2 acting agent is one of the agents described herein. For example, in certain embodiments, the HER2 acting agent is trastuzumab. In certain embodiments, the chemotherapeutic agent is paclitaxel.

Importance of HER2 and p95 in Breast Cancer

Breast cancer is among malignancies with remarkably high risk of brain relapse. Tsukada, Y. et al., Central nervous system metastasis from breast carcinoma. Autopsy study. *Cancer* 52:2349-2354 (1983); Schouten, L. J. et al., Incidence of brain metastases in a cohort of patients with carcinoma of the breast, colon, kidney, and lung and melanoma. Cancer 94:2698-26705 (2002). Brain metastases accompanying breast cancer are associated with poor prognosis, seriously affect quality of life and are relatively resistant to systemic therapies. Particularly high risk of brain relapse is associated with overexpression or amplification of HER2 gene. Hicks, D. G. et al., Breast cancers with brain metastases are more likely to be estrogen receptor negative, express the basal cytokeratin CK5/6, and overexpress HER2 or EGFR. *Am J Surg Pathol.* 30:1097-1104 (2006); Gabos, Z. et al. Prognostic significance of human epidermal growth factor receptor positivity for the development of brain metastasis after newly diagnosed breast cancer. *J Clin Oncol.* 24:5658-5663 (2006); Gonzalez-Angulo, A. M. et al., Central nervous system metastases in patients with high-risk breast carcinoma after multimodality treatment. *Cancer.* 101:1760-1766 (2004).

Currently, the standard component of systemic therapy in HER2-positive breast cancer patients is trastuzumab, a monoclonal antibody against extracellular domain of HER2 receptor. Although on average the use of trastuzumab is associated with considerable progression-free and overall survival benefit, only a fraction of HER2-positive metastatic breast cancer patients respond to this agent and a significant proportion of responders relapse within one year. Slamon, D. J. et al., Use of chemotherapy plus a monoclonal antibody against HER2 for metastatic breast cancer that overexpresses HER2. *N Engl J Med.* 344:783-792 (2001); Burstein, H. J. et al., Trastuzumab plus vinorelbine or taxane chemotherapy for HER2-overexpressing metastatic breast cancer: the trastuzumab and vinorelbine or taxane study. *Cancer* 110:965-972 (2007); Marty, M. et al. Randomized phase II trial of the efficacy and safety of trastuzumab combined with docetaxel in patients with human epidermal growth factor receptor 2-positive metastatic breast cancer administered as first-line treatment: The M77001 Study Group. *J Clin Oncol.* 23:4265-4274 (2005); Schaller, G. et al., Phase II study of capecitabine plus trastuzumab in human epidermal growth factor receptor 2-overexpressing metastatic breast cancer pretreated with anthracyclines or taxanes. *J Clin Oncol.* 25:3246-3250 (2007); Robert, N. et al., Randomized phase III study of trastuzumab, paclitaxel, and carboplatin compared with trastuzumab and paclitaxel in women with HER-2-overexpressing metastatic breast cancer. *J Clin Oncol.* 24:2786-2792 (2006). Increased HER2 total (H2T) levels have been shown to be associated with better response to trastuzumab and prolonged time to progression in advanced breast cancer patients. Lipton, A. et al. Quantitative HER2 protein levels predict outcome in fluorescence in situ hybridization-positive patients with metastatic breast cancer treated with trastuzumab. *Cancer* 116:5168-78 (2010); Toi, M. et al., Differential survival following trastuzumab treatment based on quantitative HER2 expression and HER2 homodimers in a clinic-based cohort of patients with metastatic breast cancer. *BMC Cancer* 10:56 (2010).

Importantly, due to a high molecular weight (145,000 Da) and other physical and chemical properties, trastuzumab does not cross the blood-brain barrier, and is ineffective in preventing and treating brain metastases. Pestalozzi, B. C. and Brignoli, S., Trastuzumab in CSF. *J. Clin. Oncol.* 18:2349-2351 (2000); Stemmler, J. et al., V. Brain metastases in HER2-overexpressing metastatic breast cancer: comparative analysis of trastuzumab levels in serum and cerebrospinal fluid. *J Clin Oncol.* 24:1525 (2006).

However, p95 is a truncated form of HER2 that lacks the trastuzumab binding site and is therefore thought to confer resistance to tratuzumab treatment. Sperinde, J. et al., *Clin. Cancer. Res.* 16(16): 4226-4235 (2010). Early data suggested that the presence of p95 correlates to the extent of lymph node involvement, begging the question of causality, whether p95 levels were a result of or contributed to an environment favorable to tumor dissemination. See Molina et al., *Clin. Can. Res.* 8:347-353 (2002). Using an indirect measurement of the sub-cellular localization of the HER2 intracellular domain (ICD), it has been demonstrated that intracellular distribution of the HER2 ICD, separately shown to correlate with p95 expression, trended (Fisher test p=0.057) toward a correlation with a reduction in RECIST response to trastuzumab-containing treatment. Scaltriti et al., *J. Natl Cancer Inst.* 99:628-638 (2007). Using direct antibody detection of p95, expression of p95 was found to correlate with reduced progression free survival (HR=1.9; p=0.017) and overall survival (HR=2.2; p=0.012). Sperinde et al., *Clin. Cancer. Res.* 16(16): 4226-4235 (2010).

Studies have shown that 30-50% of HER2-positive advanced breast cancer patients will develop brain relapse, with an annual risk of around 10%. See., e.g., Bendell, J. C. et al., Central nervous system metastases in women who receive trastuzumab-based therapy for metastatic breast carcinoma. *Cancer* 97:2972-2977 (2003); Shmueli, E. et al., Central nervous system progression among patients with metastatic breast cancer responding to trastuzumab treatment. *Eur J Cancer* 40:379-382 (2004); Clayton, A. J. et al., Incidence of cerebral metastases in patients treated with trastuzumab with trastuzumab for metastatic breast cancer. *Br J Cancer* 91:639-643 (2004); Lai, R. et al., The risk of central nervous system metastases after trastuzumab therapy in patients with breast carcinoma. *Cancer* 15:810-816 (2004); Lower, E. E. et al., Increased rate of brain metastases with trastuzumab therapy not associated with impaired survival. *Clin Breast Cancer* 4:114-119 (2003); Burstein, H. J. et al., Isolated central nervous system metastases in patients with HER2 overexpressing advanced breast cancer treated with first-line trastuzumab based therapy. *Ann Oncol.* 16:1772-1777 (2005); Stemmler, H. J., et al., V. Characteristics of patients with brain metastases receiving trastuzumab for HER2 overexpressing metastatic breast cancer. *Breast* 15:219-225 (2006); Gori, S. et al., Central nervous system metastases in HER-2 positive metastatic breast cancer patients treated with trastuzumab: incidence, survival, and risk factors. *Oncologist* 12:766-773 (2007); Duchnowska, R. et al., Risk factors for brain relapse in HER2-positive metastatic breast cancer patients. *Breast Cancer Res Treat.* 117:297-303 (2009).

Owing to the impaired penetration of trastuzumab through the blood-brain barrier, brain metastases frequently occur in patients with responsive or stable disease at metastatic extracranial sites. Nam, B. H. et al., Breast cancer subtypes and survival in patients with brain metastases. *Breast Cancer Res.* 10:R20 (2008); Eichler, A. F. et al., Survival in patients with brain metastases from breast cancer: the importance of HER-2 status. *Cancer* 112:2359-2367 2008). On the other hand, owing to better control of extracranial metastatic disease, trastuzumab therapy was found to delay the development of brain relapse. Dawood, S. et al., Defining prognosis for women with breast cancer and CNS metastases by HER2 status. *Ann Oncol.* 19:1242-1248 (2008); Park, I. H. et al., Trastuzumab treatment beyond brain progression in HER2-positive metastatic breast cancer. *Ann Oncol.* 20:56-62 (2009). Also, continuing treatment with trastuzumab beyond brain progression results in prolonged survival. Church, D. N. et al., Extended survival in women with brain metastases from HER2 overexpressing breast cancer. *Am J Clin Oncol.* 31:250-254 (2008); Metro, G. et al., Clinical utility of continuing trastuzumab beyond brain progression in HER-2-positive metastatic breast cancer. *Oncologist* 12:1467-1469 (2007).

Several retrospective studies have explored clinical and biological features associated with a propensity to develop brain relapse in HER2-positive advanced breast cancer patients. Reported adverse factors included the presence of visceral disease, younger age, premenopausal status, short disease-free interval after primary therapy and the negative hormone receptor status. However, the results of particular studies have been inconsistent and none of these factors or their combination could allow selecting a subset of HER2-positive advanced breast cancer patients who might benefit from active surveillance for brain relapse or from potential preventive strategies. Recently, expression of several genes was found to be associated with increased risk of brain relapse both in general population of breast cancer patients (Bos, P. D. et al., Genes that mediate breast cancer metastasis to the brain. *Nature* 459:1005-1009 (2009)) and in the HER2-positive subset (Duchnowska, R. et al., Gene expression analysis for prediction of early brain metastasis in HER2-positive breast cancer patients. *J Clin Oncol.* 26(Suppl.):45s (2008)). However, no robust molecular signature to predict brain relapse has been developed.

Using the claimed methods described herein, it has been shown for the first time that the quantitative assessment of HER2 protein or p95 protein in the primary tumor may identify HER2 positive advanced breast cancer patients with particularly high risk of developing brain metastases during trastuzumab therapy by enabling identification of subjects with relatively high levels of HER2 or p95. Using the methods described herein, it has been determined that relatively high levels of HER2 or p95 are associated with shorter time to brain metastases (TTBM). Notably, in the multivariate model, quantitative measurement of Her2 and p95, tumor grade, and time to distant progression were the only predictors of brain relapse, and only H2T and time to distant progression were statistically significant predictors of this event in the most stringently selected subset of HER-2_ patients as assessed by FISH. All other molecular and clinical factors, such as the HER-2/CEP17 ratio, HER-2 amplification, hormone receptor status, menopausal status, and age, were not statistically significant correlates of TTBM. Such differential biological effect of H2T levels or p95 levels may be due to inefficacy of trastuzumab in preventing and combating brain metastases. However, it is also possible that better control of extracranial disease with this compound may merely provide more time for the clinical manifestation of brain relapse (the effect of "unmasking"). The latter is supported by the analysis described herein taking into account progressions at other sites as competing events confirmed significant correlation between elevated levels of H2T (considered as continuous variable) and TTBM.

Methods of determining a course of treatment for a high-risk population of cancer patients are also described herein. For example, a correlation between quantitative measurements of HER2 protein expression and the risk of brain metastases in advanced HER2-positive breast cancer patients administered trastuzumab suggests that H2T assessment might potentially select patients for more personalized preventive and therapeutic strategies in this otherwise high-risk population such as, for example, small molecule drugs, chemotherapy, and/or radiation therapy. Currently several new compounds with potential prophylactic or therapeutic activity in brain metastases are being a subject of clinical investigations. In contrast to trastuzumab, small molecule drugs are more likely to traverse the blood-tumor barrier, although access to brain metastases may still be impeded. Lockman, P. R. et al., Heterogeneous blood-tumor barrier permeability determines drug efficacy in experimental brain metastases of breast cancer. *Clin Cancer Res.* 16:5664-5678 (2010). For example, lapatinib has shown promise at prevention in preclinical models and some clinical effectiveness in treating brain metastases (Gril, B. et al., Effect of lapatinib on the outgrowth of metastatic breast cancer cells to the brain. *J Natl Cancer Inst.* 100:1092-1103 (2008); Lin, N. U. et al., Phase II trial of lapatinib for brain metastases in patients with human epidermal growth factor receptor 2-positive breast cancer. *J Clin Oncol.* 26:1993-1999 (2008)). In a randomized phase III study, the addition of lapatinib to capecitabine in patients who progressed after trastuzumab therapy resulted in decreased rate of symptomatic brain relapse. Cameron, D. et al., A phase III randomized comparison of lapatinib plus capecitabine versus capecitabine alone in women with advanced breast cancer that has progressed on trastuzumab: updated efficacy and biomarker analyses. *Breast Cancer Res Treat.* 112:533-543 (2008). In addition, pazopanib has shown activity in brain metastasis prevention in mice injected with HER2 cell lines. Gril, B. et al., Pazopanib reveals a role for tumor cell B-Raf in the prevention of HER2+ breast cancer brain metastasis. *Clin Cancer Res.* 17:142-153 (2011).

As small molecule HER2-directed agents gain approval for use earlier in the progression of breast cancer, quantitative HER2 measurements using the methods disclosed herein will be useful in guiding patient care.

EXAMPLES

Example 1: Analysis of Subject Samples

Study Group:

This study was approved by the Ethics Committee of the Medical University in Gdan'sk, the coordinating center. Patients were identified through computerized hospital systems, protocol enrollment lists, or by manual search. A study group included a consecutive series of HER2-positive (IHC 3+, or IHC 2+ and FISH-positive), pathologically confirmed, advanced breast cancer patients from 9 Polish institutions. All patients received at least one dose of trastuzumab with or without chemotherapy (typically taxanes, vinorelbine, or capecitabine) between December 2000 and July 2010. The line of therapy during which trastuzumab was first administered was not recorded, although the median time from diagnosis of metastatic disease to the initiation of trastuzumab was 3.4 months (range, 0-49 months). This delay resulted from the fact that a substantial proportion of patients received trastuzumab as a second-line or subsequent line of therapy in the metastatic setting. Because the time from diagnosis of metastatic disease to the initiation of trastuzumab did not correlate with the time to brain metastasis (TTBM) (p=0.7), this factor was not used for stratification. The majority of patients remained on trastuzumab treatment until progression, three patients terminated trastuzumab administration earlier as a result of the occurrence of excessive toxicity or personal decision, and 20 patients continued trastuzumab therapy beyond progression.

A total of 164 HER2-positive advanced breast cancer patients were identified initially, 22 of whom were subsequently removed from the analysis due to pre-existing brain metastases (n=6) or because they received trastuzumab in the adjuvant setting (n=16), leaving a study cohort of 142 patients (Table 1).

The following information was extracted from the medical records: date of diagnosis of breast cancer, previous local and systemic therapy, date and type of first progression (local, regional, distant), date of diagnosis of metastatic disease, dominant site of metastatic disease (soft tissue, bone, viscera), date of diagnosis of brain metastasis, dates on which trastuzumab was received, date of first progression while on trastuzumab therapy, and date of death or last follow-up visit. For tumors involving more than one category, the dominant site of distant disease was classified by the category associated with the worst prognosis, irrespective of the extent of involvement, in the following order of increasing gravity: soft tissue, bones, viscera. Because of the retrospective nature of this study, tumor staging was performed using the American Joint Committee on Cancer/ Union for International Cancer Control classification from 1997. The brain metastases included radiographically confirmed (computed tomography or magnetic resonance imaging) parenchymal brain lesions. No screening for occult brain lesions was performed; therefore, all metastases were symptomatic or detected accidentally. Follow-up information was extracted from medical records and tumor registries. Data were collected and stored using Microsoft Excel.

The median follow-up time was 68 months (range, 7-144 months) from the initial diagnosis of breast cancer, 34 months (range, 4-121 months) from the first occurrence of metastatic disease and 29 months (range, 1-115 months) from the initiation of trastuzumab-containing therapy. The median time from the initial diagnosis to first distant relapse was 22 months (range 0-103 months) and the median time of trastuzumab therapy was 10 months (range, 1-115 months).

TABLE 1

Subject Characteristics

| Characteristic | Category | All Subjects (N = 142) | | No BM (N = 93) | | BM (N = 49) | |
|---|---|---|---|---|---|---|---|
| | | N | % | N | % | N | % |
| Menopausal status | post-menopausal | 78 | 55 | 52 | 56 | 26 | 53 |
| | pre-menopausal | 64 | 45 | 41 | 44 | 23 | 47 |
| Dominant metastatic site | viscera | 89 | 63 | 20 | 22 | 8 | 16 |
| | soft tissue | 28 | 20 | 20 | 22 | 4 | 8 |
| | bone | 24 | 17 | 52 | 56 | 37 | 76 |
| | unknown | 1 | 1 | 1 | 1 | 0 | 0 |
| Metastatic Type | at diagnosis | 14 | 10 | 9 | 10 | 5 | 10 |
| | recurrent | 18 | 18 | 84 | 90 | 44 | 90 |
| ER | positive | 55 | 39 | 40 | 43 | 15 | 31 |
| | negative | 87 | 61 | 53 | 57 | 34 | 69 |
| PgR | positive | 43 | 30 | 29 | 31 | 14 | 29 |
| | negative | 95 | 67 | 63 | 68 | 32 | 65 |
| | unknown | 4 | 3 | 1 | 1 | 3 | 6 |
| Grade | G3 | 85 | 60 | 49 | 53 | 36 | 73 |
| | G1 + G2 | 57 | 40 | 44 | 47 | 13 | 27 |
| Pathology Type | ductal | 127 | 89 | 84 | 90 | 43 | 88 |
| | lobular | 4 | 3 | 2 | 2 | 2 | 4 |
| | other | 3 | 2 | 2 | 2 | 1 | 2 |
| | unknown | 8 | 6 | 5 | 5 | 3 | 6 |
| HER2 protein (HERmark H2T)$^a$ | positive | 109 | 77 | 62 | 67 | 47 | 96 |
| | equivocal | 7 | 5 | 7 | 8 | 0 | 0 |
| | negative | 26 | 18 | 24 | 26 | 2 | 4 |
| FISH/CEP17 | >2.0 | 117 | 82 | 73 | 78 | 44 | 90 |
| | ≤2.0 | 21 | 15 | 18 | 19 | 3 | 6 |
| | unknown | 4 | 3 | 2 | 2 | 2 | 4 |
| Age at progression (yrs) | median | 53 | | 54 | | 50 | |
| | range | 25-79 | | 25-79 | | 33-72 | |

HER2+ Classification:

HER2-positive status was determined using semiquantitative immunohistochemistry (IHC) at the institutions participating in the study. HER2 gene copy number assessment using FISH was performed centrally at the Department of Biology and Genetics, Medical University of Gdansk, Poland. Gene amplification was defined as a FISH ratio (HER2/centromeric probe for chromosome 17 [CEP17] ratio) of more than 2.0. The cutoffs used to categorize subjects as HER2 FISH positive, HER2 FISH equivocal, and HER2 FISH negative were 1.8 and 2.2, respectively. Expression of estrogen receptor (ER) and progesterone receptor (PR) was determined using IHC, with 10% of nuclear staining considered as a positive result.

VeraTag® Assays:

Quantitative HER2 protein levels (units of relative fluorescence per mm$^2$ tumor (RF/mm$^2$ tumor)) were measured using the HERmark® assay as described by Lipton et al., Quantitative HER2 protein levels predict outcome in fluorescence in situ hybridization-positive patients with metastatic breast cancer treated with trastuzumab. *Cancer* 116: 5168-78 (2010) and Larson, J. S. et al., Analytical validation of a highly quantitative, sensitive, accurate, and reproducible assay (HERmark®) for the measurement of HER2 total protein and HER2 homodimers in FFPE breast cancer tumor specimens. *Patholog Res Int.* 2010:814176 (2010). See FIG. 1A. The cutoffs used to categorize subjects as HER2 positive, HER2 equivocal, and HER2 negative using the HERmark® assay were 10.5 and 17.8, respectively. Quantitative p95 protein levels (RF/mm$^2$) were measured using the VeraTag assay format illustrated in FIG. 1B, and as described in Sperinde, J. et al., *Clin. Cancer. Res.* 16(16): 4226-4235 (2010).

Tumor Staging:

Due to the retrospective nature of this study, tumor staging was performed using AJCC/UICC classification from 1997. Metastatic lesions were grouped into three categories: soft tissue, bones and viscera. For tumors involving more than one category, dominant site of distant disease was classified by the category associated with the worst prognosis, irrespective of the extent of involvement, in the following order of increasing gravity: soft tissue, bones, viscera. No screening for occult brain lesions was performed; therefore all metastases were symptomatic or detected accidentally.

Time to Brain Metastasis:

The OS time was calculated from the initiation of trastuzumab-containing treatment to death (from any cause) or was censored at the end of follow-up. The Kaplan-Meier method was used to estimate the probability of brain metastases over time. p-values were calculated for the univariate analysis using the log-rank test with stratification where indicated. Cox models were used for multivariate analysis with stratification where indicated. Cox models were also used to estimate the hazard ratio (HR) and its confidence interval (CI). In the multivariate Cox models and in the univariate Cox model assessing this particular variable, time to non-brain progression was used as a time-dependent variable to examine the effect of other types of progression on the risk for brain metastases. Analyses controlling for the competing risks of death (on brain relapse and disease recurrence at all other sites) were performed by the method of subdistribution of competing risks as described by Fine, J. P. and Gray, R. J., A proportional hazards model for the subdistribution of a competing risk. *JASA.* 94:496-509 (1999). p-values than 0.05 were considered significant. Statistical analyses were prespecified to the extent possible in a statistical analysis plan and were performed independently by separate teams at Monogram Biosciences, Inc. (South Francisco, Calif.) and International Drug Development Institute (IDDI), Inc. (Louvain-la-Neuve, Belgium). Any discrepancies were resolved by agreement among the clinical team in Poland and the statistical teams at Monogram and IDDI.

Brain Metastases and Elevated HER2:

In total, 49 of 142 patients (35%) developed symptomatic brain relapse. Among those 49 patients, the median TTBM was 13 months (95% CI, 9-18 months). After start of trastuzumab treatment, brain metastases occurred at the time of first metastatic progression in 20 patients, including 17 patients who developed brain relapse during trastuzumab treatment. The remaining 29 patients developed brain relapse after discontinuation of trastuzumab treatment. Cumulative 1-year, 2-year and 3-year risk of developing brain relapse was 19%, 30% and 46%, respectively (95% CI, 12%-25%, 22%-39%, and 34%-58%, respectively). The median time from disease dissemination to brain relapse was 38 months (range, 1-50 months). The median overall survival from the initial diagnosis of breast cancer in the overall population was 32 months (range, 1-67 months). The median OS time from the initiation of trastuzumab therapy in the overall population was 32 months (95% CI, 28-43 months), with median OS of 28 months (95% CI, 16-32 months) and 40 months (95% CI, 28-66 months) in the subgroups of patients who did and did not develop brain metastasis, respectively." Please indicated which sentence should be included.

Figure 3:
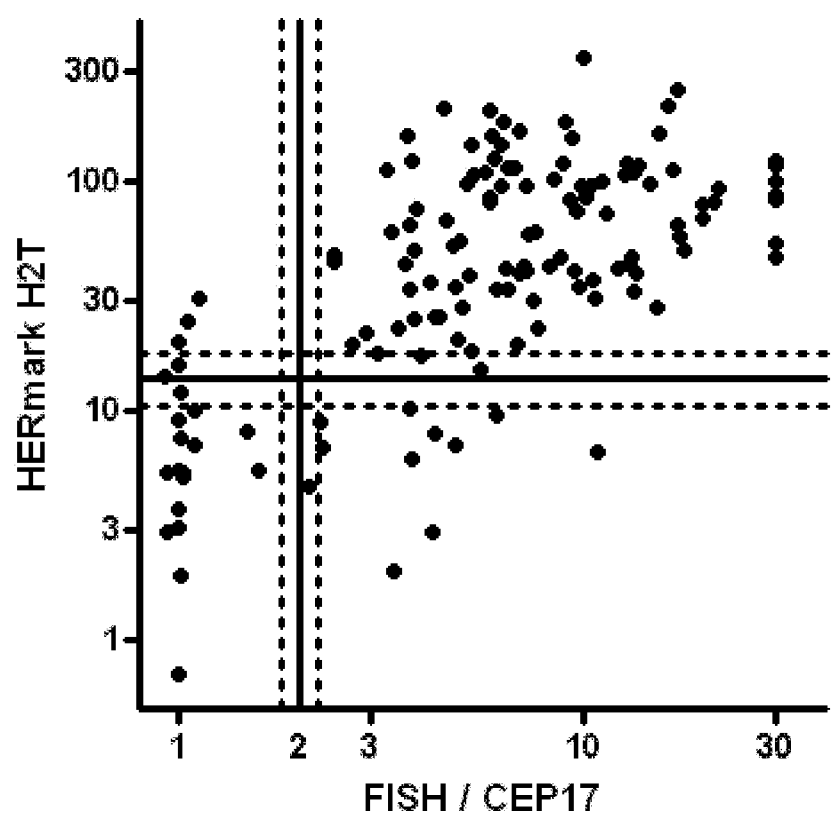
FIG. 3 is a graph illustrating the relationship between quantitative HER2 protein as measured by H2T (RF/mm$^2$ tumor) in a HERmark® assay and HER2 gene copy number per centromere 17 as measured by HER2 FISH.

HER2 amplification was found in 117 of the 138 cases analyzable using FISH (85%). The quantitative HER2 protein level (H2T) as determined by VeraTag® assay showed 86% concordance (κ=0.55) with HER2/CEP17 ratio (considering negative, equivocal, and positive categories for both H2T and FISH) (see FIG. 3; n=138). Thus, the two assays classified tumors similarly with regards to HER2 status.

Example 2: HER2 Levels Correlate with TTBM

Twelve correlates of TTBM were explored for all subject and those subjects determined to be HER2-FISH positive (Tables 2 and 3, respectively), including (a) commonly used clinical variables (age, menopausal status, dominant site of metastatic disease, estrogen receptor [ER] and progesterone receptor [PgR] levels, tumor grade, HER2 status by conventional HER2 FISH measurement), (b) time to non-brain progression, (c) the novel measurement of continuous HER2 protein level (H2T), considered as a categorical variable using a specific cutoff and also as a continuous variable, and (d) the novel measurement of p95 protein level using a predetermined cutoff.

A higher H2T measurement (assessed either as a continuous variable or as a categorical variable using defined cutoffs) was significantly correlated with a shorter TTBM in the entire HER-2 positive patient population (defined as HER-2 positive either by IHC 3+ or by FISH ratio>2.0). Two other variables that similarly correlated with TTBM are tumor grade and time from initiation of trastuzumab therapy to non-brain first progression. The hazard ratio (HR) between previously defined H2T positive and H2T negative groups (see Table 2 notation) was 5.6 (p=0.007). However, the so defined H2T-negative group in the study group was small (n=26). The best discriminating H2T cutoff value was found to be 50 RF/mm$^2$, with a HR=2.6 (p=0.001). Of note, this value was close to the median H2T of 58 RF/mm$^2$. Continuous H2T was also significantly correlated with TTBM (p=0.013), indicating a proportional rise in risk of brain metastases across the entire range of H2T. In contrast to this, neither the cutoff at FISH/CEP17=2.0 nor continuous FISH/CEP17 correlated with TTBM (p=0.28 and 0.15, respectively).

As noted above, both H2T and tumor grade were univariate correlates of TTBM. To confirm that H2T impacted TTBM independent of grade, the analyses were repeated with tumor grade as a stratification factor. Stratifying for grade, the HR for H2T at a cutoff of 50 RF/mm$^2$ was still significant (HR=2.2; p=0.013), although the correlation of continuous H2T with TTBM in the entire population was only trending (p=0.070).

A competing risks analysis was performed to confirm that the occurrence of death was not impeding the ability to accurately measure the correlation of H2T with TTBM. Controlling for death, H2T remained a significant correlate of TTBM using both the H2T=50 RF/mm$^2$ cutoff (HR, 2.7; p=0.0009) and a continuous H2T (HR, 2.7; p=0.0066) with HRs similar to or slightly higher than those calculated without controlling for death (Table 2) (HRs of 2.6 and 2.3, respectively). H2T assessed either as a continuous variable or as a categorical variable using defined cutoffs was not correlated with OS in this patient population. This observation may be due to the small size of the HER2 negative subgroup.

The symbols as set forth in Tables 2 and 3 below refer to the following:

a. Test for significant difference between any of the three categories of viscera, bone and soft tissue.
b. Time to non-brain progression used as a time-dependent variable to examine effect of other progressions on risk of brain metastases.
c. Grades 1 and 2 were combined because there was only three Grade 1 cases.
d. VeraTag® HER2 positive status is defined as H2T>17.8, and VeraTag® HER2 negative is defined as H2T≤10.5, with equivocal in between these two limits. These cutoffs were previously found to coincide with central lab determined 95th percentile of HER2-negatives and 5th percentile of HER2-positives. See Huang et al., *Amer. J. Clin. Pathol.* 134:303-311 (2010).
e. Insufficient number of events to estimate hazard ratio. There were four cases with unknown PgR, four cases with unknown FISH and seven cases where FISH spots were too numerous and clustered to make a reliable count.

TABLE 2

Univariate analysis of time to brain metastases - All Subjects

| Variable | Category | Events/N (%) | Unstratified HR | Unstratified p-value | Stratified by Grade HR | Stratified by Grade p-value |
|---|---|---|---|---|---|---|
| Age | continuous | 49/142 (35%) | 0.99 | 0.6 | 0.99 | 0.7 |
| Menopausal (MP) status | post-MP | 26/78 (33%) | 0.97 | 0.9 | 0.94 | 0.8 |
| | pre-MP | 23/64 (36%) | | | | |
| Dominant metastatic site | multiple[a] | 49/141 (35%) | — | 0.095[a] | — | 0.088[a] |
| ER | positive | 15/55 (27%) | 0.75 | 0.4 | 0.86 | 0.6 |
| | negative | 34/87 (39%) | | | | |
| PgR | positive | 14/43 (33%) | 1.1 | 0.7 | 1.3 | 0.4 |
| | negative | 32/95 (34%) | | | | |
| Grade | G3 | 36/85 (42%) | 2.4 | 0.007 | — | — |
| | G1 + G2[c] | 13/57 (23%) | | | | |
| HER2 protein (HERmark® H2T) | positive[d] | 47/109 (43%) | 5.6 | 0.007 | 4.4 | 0.029 |
| | negative[d] | 2/26 (8%) | | | | |
| FISH/CEP17 | >2.0 | 44/117 (38%) | 1.9 | 0.28 | 1.4 | 0.6 |
| | ≤2.0 | 3/21 (14%) | | | | |
| Log (H2T) | continuous | 49/142 (35%) | 2.3 | 0.013 | 1.9 | 0.070 |
| Log (FISH/CEP17) | continuous | 45/131 (34%) | 1.7 | 0.25 | 1.4 | 0.5 |
| HER2 protein (H2T) | H2T > 50 | 32/65 (49%) | 2.6 | 0.001 | 2.2 | 0.013 |
| | H2T ≤ 50 | 17/77 (22%) | | | | |
| HER2 protein (H2T) | H2T > median (44) | 33/71 (46%) | 2.3 | 0.005 | 1.9 | 0.044 |
| | H2T ≤ median (44) | 16/71 (23%) | | | | |
| Time to non-brain progression[b] | continuous | 49/142 (35%) | 2.5 | 0.006 | 2.4 | 0.010 |

TABLE 3

Univariate analysis of time to brain metastases - HER2 FISH-Positive

| Variable | Category | Events/N (%) | Unstratified HR | Unstratified p-value | Stratified by Grade HR | Stratified by Grade p-value |
|---|---|---|---|---|---|---|
| Age | continuous | 44/117 (38%) | 1.0 | 0.9 | 1.0 | 1.0 |
| Menopausal (MP) status | post-MP | 23/63 (37%) | 0.94 | 0.8 | 0.93 | 0.8 |
| | pre-MP | 21/54 (39%) | | | | |
| Dominant metastatic site | multiple[a] | 44/116 (38%) | — | 0.10[a] | — | 0.12[a] |
| ER | positive | 14/40 (35%) | 1.0 | 0.9 | 1.1 | 0.9 |
| | negative | 30/77 (39%) | | | | |
| PgR | positive | 13/35 (37%) | 1.4 | 0.4 | 1.5 | 0.22 |
| | negative | 28/79 (35%) | | | | |
| Grade | G3 | 33/73 (45%) | 2.2 | 0.022 | — | — |
| | G1 + G2[c] | 11/44 (25%) | | | | |
| HER2 protein (HERmark H2T) | positive[d] | 44/103 (43%) | —[e] | —[e] | —[e] | —[e] |
| | negative[d] | 0/11 (0%) | | | | |

TABLE 3-continued

Univariate analysis of time to brain metastases - HER2 FISH-Positive

| Variable | Category | Events/N (%) | Unstratified HR | Unstratified p-value | Stratified by Grade HR | Stratified by Grade p-value |
|---|---|---|---|---|---|---|
| FISH/CEP17 | >2.0 | — | — | — | — | — |
|  | ≤2.0 |  |  |  |  |  |
| Log (H2T) | continuous | 44/117 (38%) | 3.0 | 0.008 | 2.8 | 0.022 |
| Log (FISH/CEP17) | continuous | 42/110 (38%) | 1.4 | 0.6 | 1.2 | 0.7 |
| HER2 protein (H2T) | H2T > 50 | 31/63 (49%) | 2.6 | 0.003 | 2.3 | 0.014 |
|  | H2T ≤ 50 | 13/54 (24%) |  |  |  |  |
| HER2 protein (H2T) | H2T ≥ median (58) | 30/59 (51%) | 2.4 | 0.006 | 2.1 | 0.021 |
|  | H2T < median (58) | 14/58 (24%) |  |  |  |  |
| p95 protein | p95 > 2.8 | 30/69 (43%) | 2.0 | 0.037 | 1.7 | 0.12 |
|  | p95 ≤ 2.8 | 14/48 (29%) |  |  |  |  |
| Time to non-brain progression[b] | continuous | 44/117 (38%) | 2.4 | 0.015 | 2.2 | 0.025 |

Example 3: H2T and p95 Levels Correlate with TTBM in a FISH-Positive Population In order to prevent data skewing due to false IHC HER2 positives, parallel analysis was performed in a subset of 117 subjects whose HER2 FISH-positive status was centrally determined (Table 3). In this group, H2T (assessed as a continuous variable and using defined cutoffs, with or without stratification by tumor grade) was significantly correlated with TTBM, whereas continuous FISH/CEP17 was not (p≥0.6). Within the HER2 FISH-positive population, patients with tumors determined to have above-median HER2 protein levels (H2T=58 RF/mm$^2$) were more than 2-fold more likely to develop brain metastases than those with below median HER2 protein without (HR, 2.4; p=0.006) and with (HR, 2.1; p=0.021) grade stratification (see FIG. 4A). A slightly larger difference was seen for the cutoff value of 50 RF/mm$^2$ without (HR=2.6; p=0.003) and with (HR=2.3; p=0.014) grade stratification (see FIG. 4B). In contrast, patients with tumors determined to have HER2 gene amplification above or below the median (HER2/CEP17=6.9) had similar likelihood of developing brain metastases both without (HR=1.3; p=0.4) and with (HR=1.3; p=0.5) grade stratification (see FIG. 4C). Similar results were also observed with other FISH HER2/CEP17 cutoffs (data not shown).

High levels of p95 expression has previously been shown to correlate with poor outcomes in trastuzumab-treated breast cancer. Sperinde, J. et al., *Clin. Cancer. Res.* 16(16): 4226-4235 (2010). Sperinde et al. used a p95 cutoff of 2.8 RF/mm$^2$ for a VeraTag® assay format as set forth in FIG. 1B to stratify subjects into high p95 expressing and low p95 expression groups. In the current cohort, p95 expression above the p95 cutoff of 2.8 RF/mm$^2$ was found to correlate with a shorter time to brain metastasis (Table 3 and FIG. 4D). The 2.8 RF/mm$^2$ cutoff was also found to be the optimal cutoff for differentiating high and low risk of brain metastasis in this set. Within the HER2 FISH-positive population, patients with tumors determined to have above-cutoff p95 protein levels (p95>2.8 RF/mm$^2$) were about 2-fold more likely to develop brain metastases than those with below the p95 protein cutoff without (HR, 2.0; p=0.037) and with (HR, 1.7; p=0.12) grade stratification (see FIG. 4D). This analysis had previously been performed on this same set of subject samples before macrodissection to remove non-tumor contaminants could be accomplished, and the correlation with time to brain metastasis was found to be consistent. See U.S. Provisional Appl. No. 61/488,028, FIG. 2D.

Figure 4:
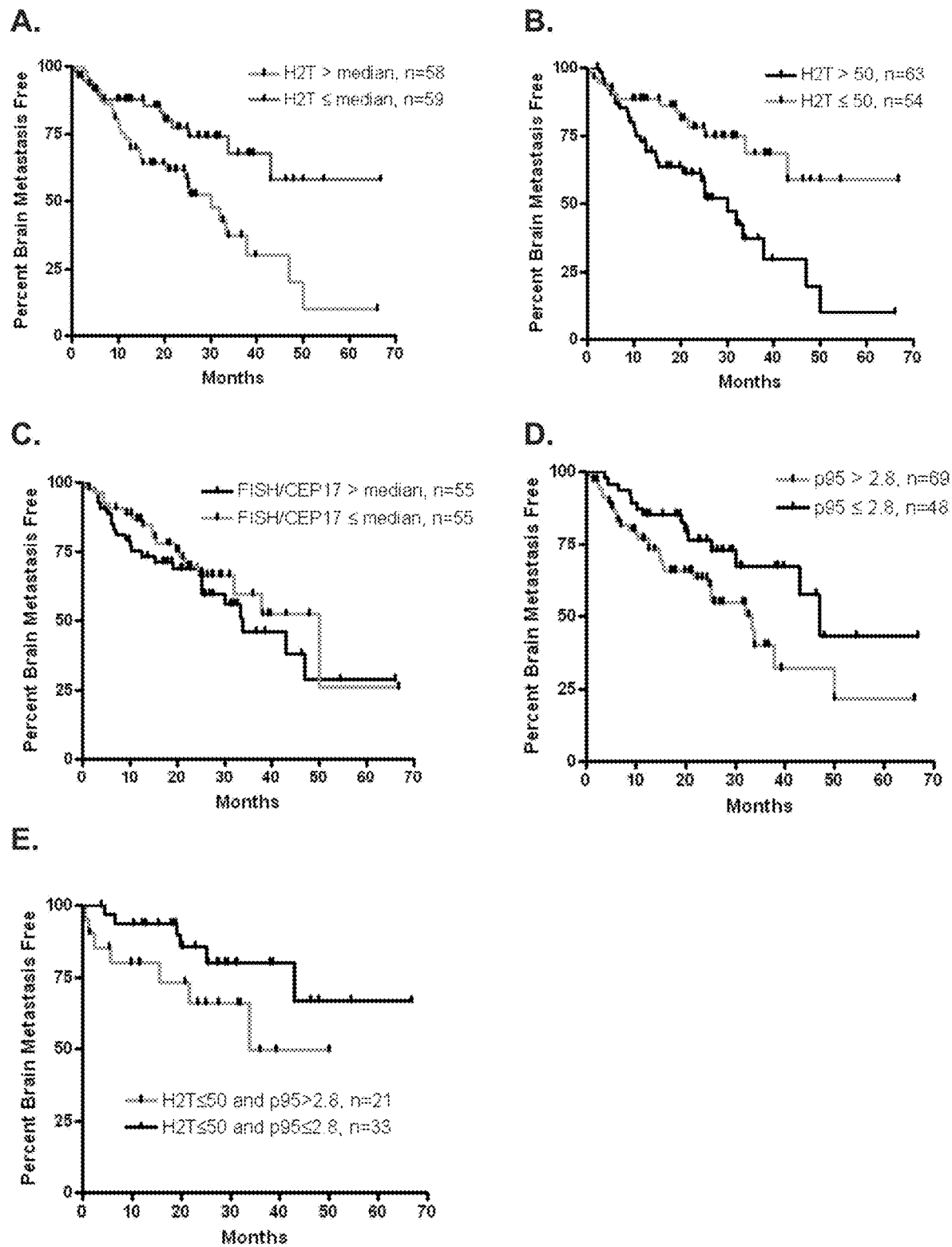
FIG. 4 shows Kaplan Meier plots illustrating time to brain metastases in months based on different protein marker categories according to embodiments of the invention. Panel A shows data based on quantitative HER2 levels, wherein subjects with a H2T level above (grey line) and below (black line) the median are compared. Panel B shows data based on quantitative HER2 levels in subjects with levels of HER2 above (black line) and below (grey line) the optimal cutoff of H2T. Panel C shows data based on HER2 FISH analysis, where subjects with levels above (black line) vs. below (grey line) the median are compared. Panel D shows data based on quantitative p95 levels, wherein subjects with a p95 level above (grey line) and below (black line) an optimal p95 cutoff are compared. Panel E shows data based on quantitative p95 levels within the low HER2 group identified in Panel B to illustrate the independence of H2T and p95 as significant biomarkers.

In order to determine if the H2T cutoff and p95 cutoff are independent variables, the subset of patients who were determined to have HER2 FISH-positive status and H2T expression below the 50 RF/mm$^2$ cutoff were further assessed based on p95 expression levels. As shown in FIG. 4E, subjects with levels of p95 below the p95 cutoff had a longer TTBM than those with p95 levels above the p95 cutoff (HR=2.5, p=0.10). Thus, use of p95 as a variable enabled identification of additional patients at risk for brain metastasis as compared to H2T measurements alone. The small number of patients assessed likely negatively impacted the p value.

A competing risks analysis was performed to confirm that the occurrence of death was not impeding the ability to accurately measure the correlation of H2T with TTBM. Controlling for death, H2T was still found to be a significant correlate of TTBM for both the H2T=50 RF/mm$^2$ cutoff (HR=2.7; p=0.0009) and continuous H2T (HR=2.7; p=0.0066), with HRs similar to or slightly higher than those calculated without controlling for death (Table 2: HR=2.6 and HR=2.3, respectively). Additionally, the p95 cutoff was still found to correlate with TTBM while controlling for death (HR=1.7, p=0.089).

Figure 5:
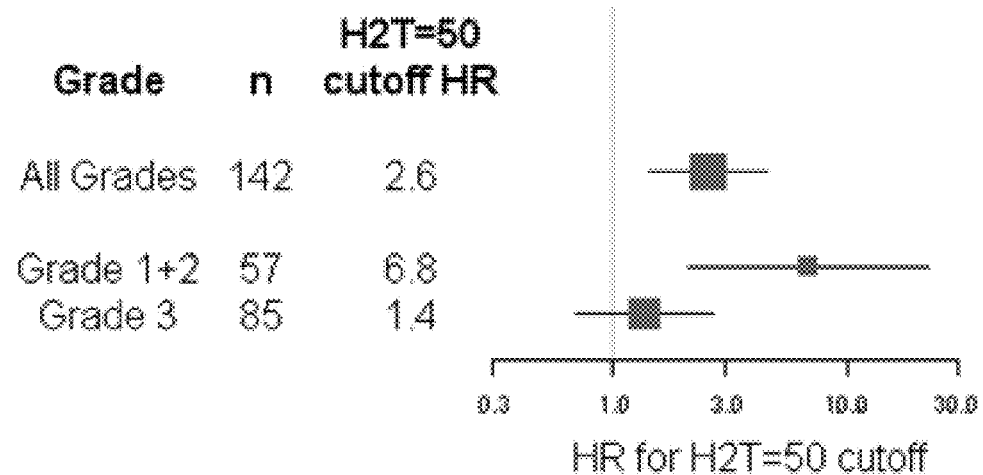
FIG. 5 illustrates the effect of quantitative HER2 levels in view of tumor grade on time to brain metastases according to embodiments of the invention. Panel A shows a Forest plot illustrating the hazard ratio determined based on quantitative HER2 levels and tumor grade. Panel B is a Kaplan-Meier plot illustrating the time to brain metastases in months when HER2 levels in different tumor grades are compared.
Figure 5:
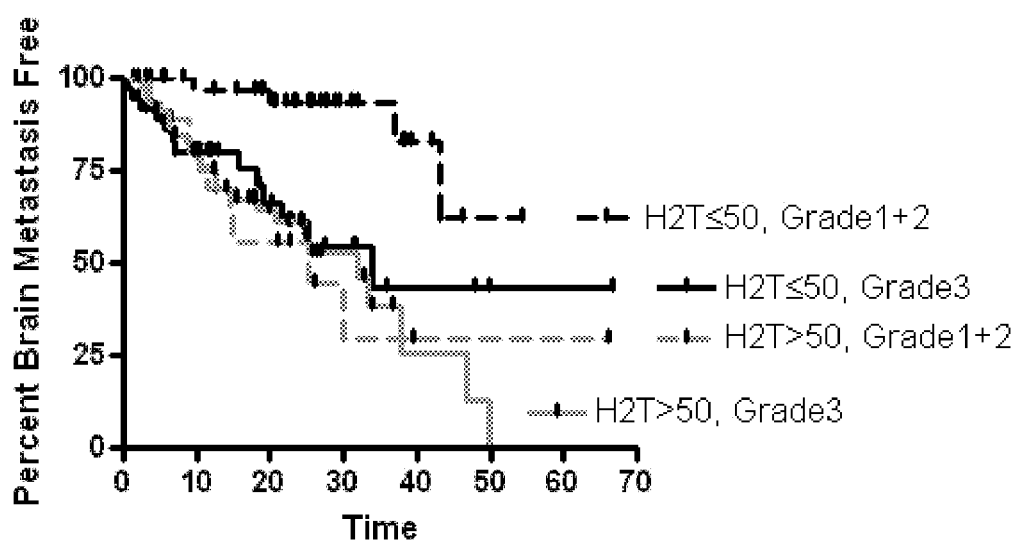

Example 4: Effect of Tumor Grade on H2T Correlation with Time to Brain Metastases Because tumor grade was found to be a significant correlate of TTBM on univariate analysis, and it had some effect on the HR CIs for H2T when used as a stratification factor, we separately examined the correlation of H2T with TTBM in the subsets of patients with grade 1-2 and grade 3 tumors. A Forest plot with hazard ratios for the H2T=50 RF/mm$^2$ cutoff for each of the grade subgroups is shown in FIG. 5A. The correlation between H2T and TTBM was stronger in the grade 1-2 subset, consistent with an interaction between H2T and tumor grade (p=0.025). A Kaplan- Meier plots for the four subgroups defined by the H2T=50 RF/mm² cutoff and two grade categories is shown in FIG. 5B. TTBM for the four subgroups defined by the H2T cutoff of 50 RF/mm2 and two grade categories (combined grades 1-2 versus grade 3) showed similar outcomes for three of the groups (H2T low-grade 3, H2T high-grade 1-2, H2T high-grade 3) as compared to that of the H2T low-grade 1-2 subset, which had a significantly lower likelihood of developing brain metastases (log-rank p=0.0012 for comparison of the four subgroups; HR=5.7; p=0.0001 for [H2T>50 RF/mm² or grade 3] vs. [H2T<50 RF/mm² and grade<3]). A univariate Cox model estimated an HR of 0.17 for the H2T low-grade 1-2 patients compared with patients in the three other groups (p=0.0001). Even though the log-rank comparison of the four subgroups (with three degrees of freedom) was also significant (p=0.0012), this result should be interpreted cautiously given the multiple comparisons that are possible among these four subsets.

Figure 6:
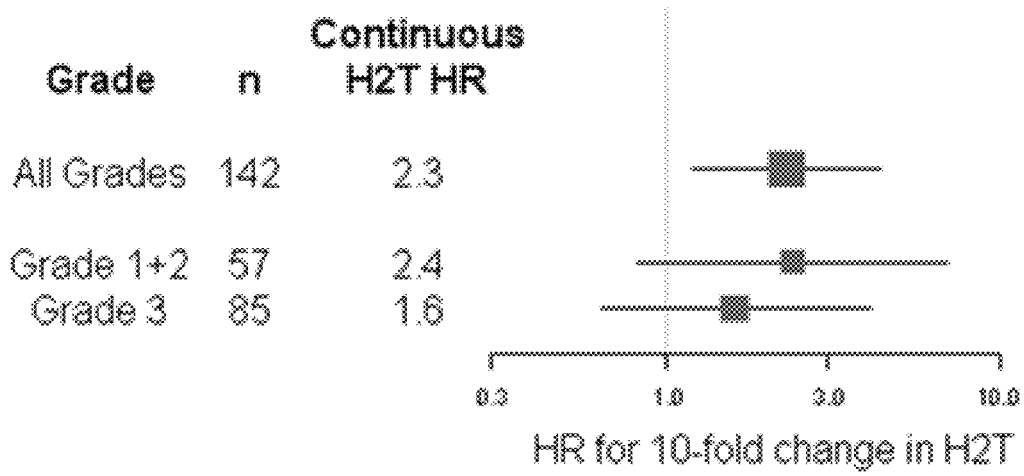
FIG. 6 illustrates the effect of quantitative HER2 levels in view of tumor grade on time to brain metastases according to embodiments of the invention. Panel A is a Forest plot illustrating the hazard ratio based on quantitative continuous HER2 levels (no cutoff) and tumor grade. Panel B is a Forest plot illustrating the hazard ratio based on quantitative continuous HER2 levels and tumor grade within the subset of HER2 FISH positive subjects.
Figure 6:
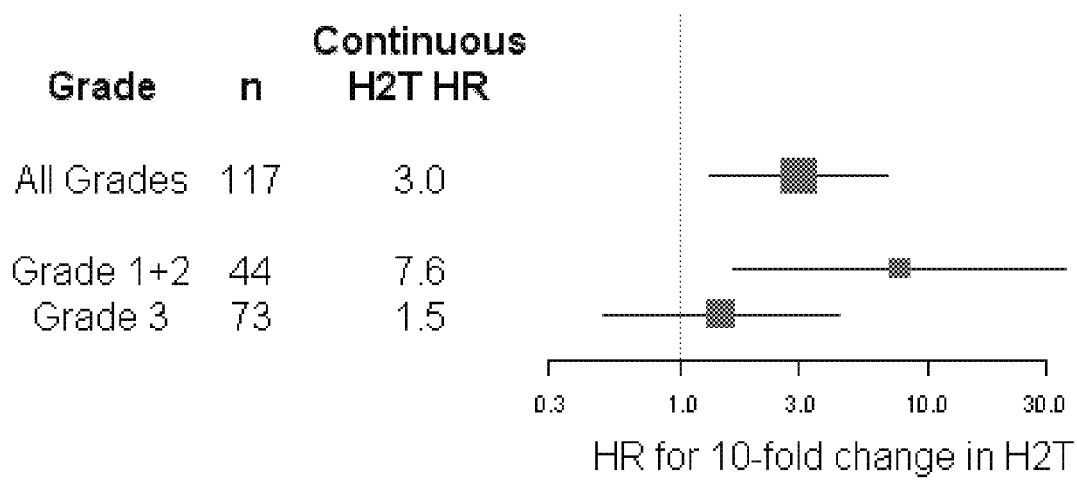

To examine whether this was a general phenomenon across the entire range of H2T, a similar analysis was performed to examine the correlation of continuous H2T with TTBM within the two subgroups of grades 1+2 or grade 3. As shown in FIG. 6A, there was no statistical difference in the correlation between continuous H2T and TTBM for the different grade groups (interaction p-value=0.6). However, as shown in FIG. 6B, a trend toward a stronger correlation between continuous H2T and TTBM was observed in the grade 1-2 patient subgroup than in the grade 3 patient subgroup in the subset of patients who were confirmed centrally as HER-2 positive by FISH (interaction p=0.10).

Example 5: The Impact of Progression Other than Brain Metastases

It has previously been demonstrated that a shorter time to any distant relapse in HER2-positive advanced breast cancer patients was associated with increased risk of developing brain metastases. Similarly, using the methods of the current invention, progression treated as a time dependent variable was found to be significantly associated with TTBM in univariate analysis (Tables 2 and 3). To further examine the correlation between other sites of progression/metastasis and TTBM, multivariate models were tested for independent correlation of TTBM with H2T, FISH/CEP17, estrogen receptor (ER), progesterone receptor (PgR), tumor grade, and progression other than brain metastases as a time-dependent variable. Multivariate models were fitted with TTBM as the outcome, H2T and the HER-2/CEP17 ratio as baseline variables, and progression other than brain metastasis as a time-dependent variable. The models were stratified by tumor grade and ER and PgR status. H2T and FISH/CEP17 were tested as continuous variables rather than using defined cutoffs to avoid potential overfitting associated with particular cutoffs.

H2T and FISH were further assessed by multivariate analysis and, aa shown in Table 4, time to non-brain progression was again found to be significantly associated with TTBM while controlling for other indicated variables. In the subset of patients who were HER2 FISH-positive, a continuous H2T level (HR=3.3; p=0.024) and time to non-brain progression (HR=2.9; p=0.0056) were found to independently correlate with TTBM, whereas HER2/CEP17 was not. Similar results were found with grade stratification.

TABLE 4

Multivariate analysis of time to brain metastases

| Variable | All Subjects | | HER2+ by FISH | |
|---|---|---|---|---|
| | HR | p-value | HR | p-value |
| Log(H2T) | 2.3 | 0.071 | 3.3 | 0.024 |
| Log(FISH/CEP17) | 0.61 | 0.46 | 0.45 | 0.32 |
| Time to non-brain progression$^a$ | 3.0 | 0.0035 | 2.9 | 0.0056 |

H2T and the other clinical variables set forth in Tables 2 and 3 were also further assessed by multivariate analysis. H2T and FISH/CEP17 were tested as continuous variables rather than with cutoffs to avoid biases associated with any particular cutoff. As shown in Tables 5 and 6, time to non-brain progression was again found to be significantly associated with TTBM while controlling for other factors. In the HER2 FISH-positive subset, continuous H2T (HR=3.2; p=0.021) and time to non-brain progression (HR=3.0; p=0.0044) were found to independently correlate with TTBM. Similar results were found with grade stratification.

TABLE 5

Multivariate analysis of time to brain metastases - All Subjects

| Variable | Unstratified | | Stratified by Grade | |
|---|---|---|---|---|
| | HR | p-value | HR | p-value |
| ER | 0.60 | 0.25 | 0.62 | 0.28 |
| PgR | 1.7 | 0.24 | 1.6 | 0.28 |
| Grade | 1.7 | 0.14 | — | — |
| Log(H2T) | 2.3 | 0.068 | 2.3 | 0.071 |
| Log(FISH/CEP17) | 0.75 | 0.67 | 0.75 | 0.65 |
| Time to non-brain progression$^a$ | 3.2 | 0.0019 | 3.2 | 0.0019 |

TABLE 6

Multivariate analysis of time to brain metastases - HER2 FISH-Positive

| Variable | Unstratified | | Stratified by Grade | |
|---|---|---|---|---|
| | HR | p-value | HR | p-value |
| ER | 0.7 | 0.44 | 0.74 | 0.51 |
| PgR | 1.7 | 0.25 | 1.6 | 0.28 |
| Grade | 1.7 | 0.17 | — | — |
| Log(H2T) | 3.2 | 0.021 | 3.3 | 0.021 |
| Log(FISH/CEP17) | 0.64 | 0.56 | 0.64 | 0.56 |
| Time to non-brain progression$^a$ | 3.0 | 0.0044 | 3.0 | 0.0042 |

Example 6: HER2 Protein Level According to Dominant Metastatic Site

Figure 7:
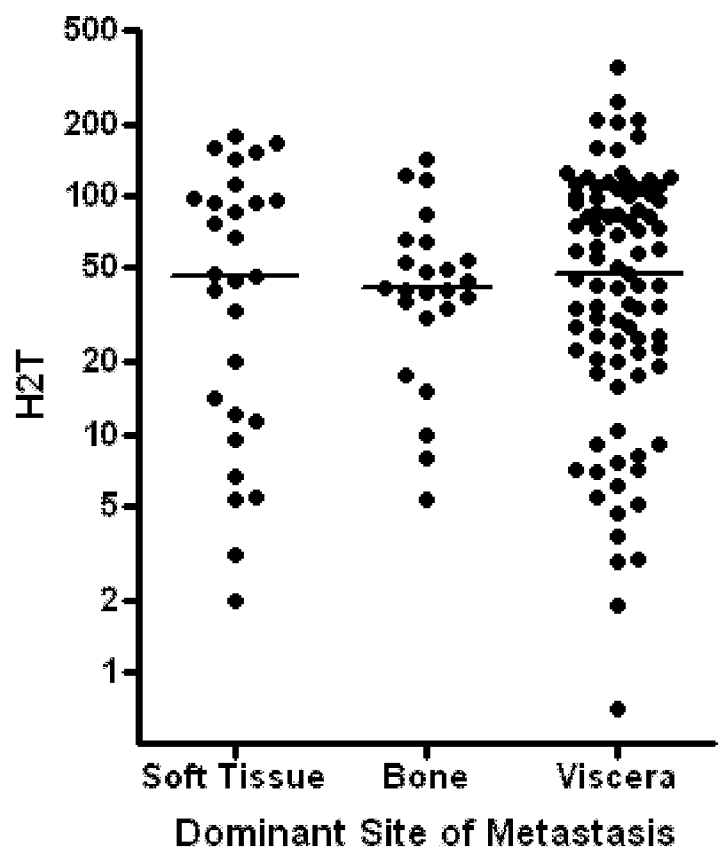
FIG. 7 is a diagram showing the dominant site of metastasis as determined by a physician at the beginning of the study and the H2T level for each of the dominant metastatic sites.

Following the finding that H2T correlated with TTBM, further analysis was conducted to determine if the occurrence of metastases at other sites was also correlated with H2T. Detailed site-specific follow up was not available for other metastatic sites, however the dominant site of metastasis were known for 141 of the 142 patients. As shown in FIG. 7, the distributions of H2T measurements were not statistically different based on the dominant metastatic site (soft tissue, bone and extracranial viscera) (p=0.9). In addition, no correlation was observed between the dominant metastatic site and TTBM (p=0.1).

While the preferred embodiments of the invention have been illustrated and described, it will be appreciated that various changes can be made therein without departing from the spirit and scope of the invention.

All printed patents and publications referred to in this application are hereby incorporated herein in their entirety by this reference.

That which is claimed is:

1. A method of treating a subject having a HER2-positive cancer, the method comprising the steps of:
   selecting a subject who has been determined to have an amount of p95-HER2 protein in a sample of the subject's HER2-positive tumor above a predetermined cutoff by:
   (a) providing a p95-HER2 monoclonal antibody produced by a hybridoma cell line having ATCC accession number PTA-9740 (p95.D9.1), PTA-9738 (p95.D3.4), or PTA-9739 (p95.D8.2);
   (b) providing a binding compound that binds to the p95-HER2 monoclonal antibody, wherein the binding compound comprises a molecular tag covalently attached thereto via a cleavable linkage;
   (c) quantifying the amount of p95-HER2 protein in a sample from the subject by the steps of (i) incubating the sample with the p95-HER2 monoclonal antibody and the binding compound, (ii) treating the sample with a cleaving agent to release the molecular tag from the binding compound, and (iii) measuring the amount of released molecular tag as indicative of the amount of p95-HER2 protein in the sample; and
   (d) comparing the amount of p95-HER2 protein in the sample determined in step (c) with the predetermined cutoff,
   wherein the predetermined cutoff comprises at least one of
   (i) a level of p95-HER2 protein expression at least two-fold greater than a control cancer cell line having a basal level of p95-HER2 expression,
   (ii) a level of p95-HER2 protein expression corresponding to at least a top $30^{th}$ percentile of p95-HER2 protein expression in a reference cohort of subjects having the HER2 positive cancer; and
   administering a HER2-acting agent and a second form of cancer treatment to the subject,
   wherein the p95-HER2 protein has a first amino acid corresponding to methionine 611 of HER2 protein.

2. The method of claim 1, wherein the predetermined cutoff comprises a level of p95-HER2 protein expression corresponding to at least a top $40^{th}$ percentile of p95-HER2 protein expression in a reference cohort of subjects having the HER2 positive cancer.

3. The method of claim 1, wherein the control cancer cell line comprises SKBR3 and/or MCF7.

4. The method of claim 1, wherein the second form of cancer treatment comprises at least one of a HER2-targeted small molecule drug, chemotherapy, or radiation therapy.

5. The method of claim 1, wherein the HER2-positive cancer of the subject has been characterized as HER2-positive based on at least one of an elevated level of HER2 gene expression, an elevated level of HER2 protein level, or HER2 gene amplification.

6. The method of claim 1, wherein the subject has been characterized as HER2-positive by quantifying the amount of HER2 in the sample using a quantitative immunoassay and determining if the amount of HER2 in the sample is above median amount of HER2 determined in the reference population of subjects having the HER2-positive cancer.

7. The method of claim 1, wherein the HER2-positive cancer of the subject comprises breast cancer.

8. The method of claim 7, wherein the HER2-positive cancer of the subject comprises primary breast cancer.

9. The method of claim 1, wherein the HER2-acting agent is a monoclonal antibody.

10. The method of claim 9, wherein the monoclonal antibody is trastuzumab.

11. The method of claim 1, wherein the subject has increased risk of metastasis as compared to a control subject that has a p95-HER2 protein amount below the predetermined cutoff.

* * * * *